United States Patent [19]

Shiosaki et al.

[11] Patent Number: 5,668,141

[45] Date of Patent: Sep. 16, 1997

[54] TRANS-2,6-,3,6-AND 4,6-DIAZA-5,6,6A,7,8,12B-HEXAHYDROBENZO[C]PHENANTHRENE COMPOUNDS AS DOPAMINE AGONISTS

[75] Inventors: Kazumi Shiosaki, Libertyville; Yu Gui Gu, Grayslake; Michael Michaelides, Highland Park, all of Ill.

[73] Assignee: Abbott Laboratories, Abbott Park, Ill.

[21] Appl. No.: 626,654

[22] Filed: Apr. 2, 1996

[51] Int. Cl.$^6$ .................. A61K 31/445; C07D 471/04
[52] U.S. Cl. ........................................ 514/285; 546/70
[58] Field of Search ................... 514/280, 285; 546/47, 70

[56] References Cited

U.S. PATENT DOCUMENTS

| | | | |
|---|---|---|---|
| 4,282,227 | 8/1981 | Brenner | 514/301 |
| 4,340,600 | 7/1982 | Brenner et al. | 514/307 |
| 5,047,536 | 9/1991 | Nichols | 546/61 |
| 5,420,134 | 5/1995 | Nichols et al. | 514/280 |

FOREIGN PATENT DOCUMENTS

| | | |
|---|---|---|
| 9324462 | 12/1993 | WIPO . |
| 9422858 | 10/1994 | WIPO . |

OTHER PUBLICATIONS

Sawaguchi et al., D1 Dopamine Receptors in Prefontal Cortex: Involvement in Working Memory; Feb. 1991, Science vol. 251.

Meltzer; Novel Approaches to the Pharmacotherapy of Schizophrenia; Drug Development Research 9:23–40 (1986).

Del Zompo, Dopamine Agonists in the Treatment of Schizophrenia; Progress in Brain Research vol. 65 (1986).

Levy; The Dopamine Theory OPF Attention Deficit Hyperactivity Disorder (ADHD) Australian and New Zealand Journal of Psychiatry 1991; 25:277–283.

Britton et al., Evidence for Involvement of Both D1 and D2 Receptors in Maintaining Cocaine Self–Administration, Parma Biochemistry & Behavior vol. 39, pp. 911–915 (1991).

Anderson et al., Thienopyridine Derivatives Identified as the First Selective, Full Efficacy, Dopamine D1 Receptor Agonists; European Journal of Pharmacology 137(1987) 291–292.

Kiguchi et al., A Route for Total Synthesis of Ergot Alkaloids Synthesis of the Desphyrrole Analogs of Methyl Lysergate, Isolysergol, and Isofumigtclavine A.; Heterocycles vol. 19, No. 10, 1982.

Effects of the D1 Agonist SKF–38393 Combined with Haloperidol in Schizophrenic Patients; Arch Gen Psychiatry vol. 47, Feb. 1990.

Muscat et al., Antidepressant–like effects of Dopamine Agonists in an Animal Model of Depression; Biol Psychiatry 1992;31:937–946.

Asin et al, Repeated D1 Receptor Agonist Treatment Blocks Cocaine–Induced Locomotor Activity and C–FOS Expression; Brain Research 637(1994) 342–344.

Reynolds, et al., Developments in the Drug Treatment of Schizophrenia; Trends in Pharmacological Sciences, 1992, 13(3), pp. 116–121.

Sibley et al., Molecular Biology of Dopamine Receptors; TIPS, 1992, 13(2) pp. 61–69.

Arnsten et al., Dopamine D1 Receptor Mechanisms in the Cognitive Performance of Young Adult and Aged Monkeys; Psychopharmacology (1994) 116:143–151.

Katz et al; Selective Effects of the D1 Dopamine Receptor Agonist, SKF 38393, on Behavior Maintained by Cocaine Injection in Squirrel Monkeys; Psychopharmacology (1992) 109;241–244.

Katerinopoulos et al., Structure Activity Relationships for Dopamine Analogs: A Review; Drugs of the Future vol. 12, No. 3 1987.

Lokhandwala; Preclinical and Clinical Studies on the Cardiovascular and Renal Effects of Fenoldopam a DA1 Receptor Agonist; Drug Devel. Research 10:123–134(1987).

Kaiser et al; Dopamine Receptors: Functions, Subtypes and Emerging Concepts; Medicinal Research Reviews vol. 5, No. 2, 145–229 (1985).

Wise et al, Brain Dopamine and Reward; Ann Rev. Psychol 1989 40:191–225.

*Primary Examiner*—C. Warren Ivy
*Assistant Examiner*—Garth M. Dahlen
*Attorney, Agent, or Firm*—Monte R. Browder

[57] ABSTRACT

A tetracyclic compound of the formula:

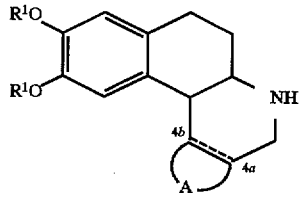

wherein A and the atoms to which it is attached comprise a pyridine ring selected from:

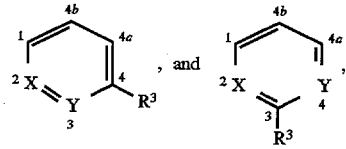

wherein $R^1$, $R^2$, and $R^3$ are specifically defined, which compounds are useful in the treatment of dopamine-related neurological, psychological and cardiovascular disorders as well as in the treatment of substance abuse and other addictive behavior disorders, cognitive impairment and attention deficit disorder, and methods for the preparation thereof.

24 Claims, No Drawings

TRANS-2,6-,3,6-AND 4,6-DIAZA-5,6,6A,7,8,12B-HEXAHYDROBENZO[C]PHENANTHRENE COMPOUNDS AS DOPAMINE AGONISTS

TECHNICAL FIELD

This invention relates to novel trans-2,6-, 3,6-and 4,6-diaza-5,6,6a,7,8,12b-hexahydrobenzo[c]phenanthrene compounds which are selective dopamine agonists useful for treating dopamine-related neurological, psychological, cardiovascular, cognitive and behavioral disorders.

BACKGROUND OF THE INVENTION

Dopamine is an important neurotransmitter in the central nervous system (CNS), where it is involved with motor function, perception, cognition, attention, arousal, motivation and emotion. Dopamine imbalance is believed to play a key role in a number of CNS-related disorders such as schizophrenia, Parkinson's disease, drug abuse, eating disorders and depression. Dopamine also has several important roles in the peripheral nervous system, such as in the control of blood to the kidneys and in autonomic ganglion transmission.

Dopamine receptors in the CNS have traditionally been divided into two general categories, designated D-1 and D-2 receptors, based on biochemical and pharmacological differences between the two receptor types. (For a review of the classification and function of dopamine receptor subtypes, see C. Kaiser and T. Jain, "Dopamine Receptors: Functions, Subtypes and Emerging Concepts", *Medicinal Research Reviews*, 5:145–229, 1985.) Recent molecular biology studies have indicated an even greater heterogeneity of dopamine receptors: the D-2, D-3 and D-4, which are classified as D-2-like, and the D-1 and D-5, which are classified as D-1-like (D. Sibley and F. Monsma, "Molecular Biology of Dopamine receptors", in TIPS, Vol. 13, pp. 61–69, 1992). Attempts to understand the physiological and pathophysiological roles of the various dopamine receptor subtypes are continuing to unveil new avenues for novel therapeutic approaches for the treatment of dopamine-related disorders.

The loss of striatal dopamine within the basal ganglia, the region of the mammalian brain that is involved with motor control, has been established as the fundamental deficit in Parkinson's disease and primary to the etiology of that disease state. This deficiency is addressed via dopamine replacement therapy, primarily with L-DOPA (3,4-dihydroxyphenylalanine), which is converted to dopamine within the brain. L-DOPA has been the cornerstone of Parkinson's disease therapy, and the successes achieved with its therapy have led to the testing of other compounds capable of eliciting the post-synaptic receptor actions of dopamine. Bromocriptine, the most widely used direct-acting dopamine agonist for the treatment of Parkinson's disease, is typically administered adjunctively with L-DOPA in order to lower dosages of the latter required to achieve the desired therapeutic response. Bromocriptine alone has been shown to relieve Parkinson's disease symptoms in some early Parkinson's disease patients, allowing for a delay in the onset of L-DOPA therapy. Chronic L-DOPA use is associated with a number of serious side-effects and limitations, such as the development of dyskinesias, severe response fluctuations (on-off phenomenon) and diminishing efficacy during treatment.

An excess of dopamine in the brain has been identified as the cause of schizophrenia, a psychiatric illness involving disturbance of thought processes, hallucinations and loss of touch with reality. Chronic abuse of stimulants, such as amphetamines, known to enhance dopaminergic activity in the brain, can lead to a paranoid psychosis that is clinically indistinguishable from classic paranoid schizophrenia, further supporting this dopamine theory of schizophrenia.

Anti-schizophrenic drugs are postulated to exert their effects by blocking the dopamine receptors (i.e., acting as receptor antagonists), and consequently preventing excess receptor stimulation (G. P. Reynolds, "Developments in the drug treatment of schizophrenia", in *TIPS*, 13:116–121, 1992). However, these antipsychotic agents frequently produce undesirable side-effects, the most common of which are the extrapyramidal effects that include bizarre involuntary movements and Parkinson-like states, as well as sedation and hypotension. Because of these often-severe side-effects and the high incidence of patients unresponsive to dopamine blocking drugs, novel and improved therapies continue to be sought.

One complement to dopamine receptor antagonists for the treatment of schizophrenia has included the use of low doses of dopamine agonists, such as apomorphine and bromocriptine (also discussed above), which have been reported to produce antipsychotic effects, possibly due to preferential activation of dopamine presynaptic receptors resulting in decreased dopaminergic activity (M. Del Zompo et al, "Dopamine agonists in the treatment of schizophrenia", *Progress in Brain Research*, 65:41–48, 1986 and H. Y. Meltzer, "Novel Approaches to the Pharmacology of Schizophrenia", *Drug Development Research*, 9:23–40, 1986). In addition, the dopamine D1-selective agonist, SKF 38393, when used in conjunction with the antipsychotic drug, haloperidol, a D-2 antagonist, has been shown to ameliorate the undesired side-effects of the haloperidol (M. Davidson, "Effects of the D-1 Agonist SKF-38393 Combined With Haloperidol in Schizophrenic Patients", *Arch Gen. Psychiatry*, 47:190–191, 1990).

Growing evidence (reviewed by R. A. Wise and P.-P. Rompre in "Brain Dopamine and Reward", *Annual Review of Psychology*, 40:191–225, 1989) suggests that dopamine also has a central role in the brain's reward system. For example, animals trained to self-administer cocaine will increase their consumption of this drug after treatment with either a D-1 or a D-2 receptor antagonist, presumably in order to maintain the elevated dopamine levels responsible for the drug's euphorigenic and reinforcing properties (D. R. Britton et al, "Evidence for Involvement of Both D1 and D2 Receptors in Maintaining Cocaine Self-Administration", *Pharmacology Biochemistry & Behavior*, 39:911–915, 1991). The D-1 agonist, SKF 38393, has also been reported to decrease food intake by rats, presumably by direct action of the drug on neural feeding mechanisms. Because of this interrelationship between dopamine and reward, dopaminergic agents would be useful for the treatment of substance abuse and other addictive behavior disorders, including cocaine addiction, nicotine addiction and eating disorders.

Affective disorders, the most common psychiatric disorders in adults, are characterized by changes in mood as the primary clinical manifestation, and result from a reduction in the central nervous system of certain biogenic amine neurotransmitters, such as dopamine, noradrenaline and serotonin. Currently-available antidepressants work primarily by raising biogenic amine neurotransmitter levels, either by inhibiting their uptake or preventing their metabolism. No antidepressant drug to date, however, can substitute for electroconvulsive shock therapy for the treatment of severe, suicidal depression. Currently-available drugs for treating affective disorders unfortunately suffer from delayed onset of action, poor efficacy, anticholinergic effects at therapeutic doses, cardiotoxicity, convulsions and the possibility of overdosing. A large number of clinically-depressed individuals remain refractory to currently available therapies. A role for direct-acting dopamine agonists in antidepressant therapy has been suggested based on the effects observed for several dopamine agonists in various animal models (R. Muscat et al., "Antidepressant-like effects of dopamine agonists in an animal model of depression", *Biological Psychiatry*, 31:937–946, 1992).

A role for dopamine has also been established in cognition and attention mechanisms. Animal studies support the role of dopamine in attention-related behaviors involving search and exploratory activity, distractibility, response rate, discriminability and the switching of attention. Treatment of cognitive impairment and attention deficit disorders via dopamine-based therapy has been proposed and is under active investigation (F. Levy, "The Dopamine Theory of Attention-Deficit Hyperactivity Disorder (ADHD)", in *Australian and New Zealand Journal of Psychiatry*, 25:277–283, (1991); T. Sawaguchi and P. S. Goldman-Rakic, "D1-Dopamine Receptors in Prefontral Cortex: Involvement in Working Memory", *Science*, 252:947–940 (1991); and A. F. T. Arnsten et al., "Dopamine D1 Receptor Mechanisms in the Cognitive Performance of Young Adult and Aged Monkeys", *Psychopharmacology*, 116:143–151 (1994)).

In addition, dopamine has been identified with a number of effects in the periphery, and has been used in the treatment of shock, congestive heart failure and acute renal failure. Stimulation of the peripheral D-1 receptors causes vasodilation, particularly in the renal and mesenteric vascular beds where large numbers of these receptors are found. The utility of dopamine has been limited, however, by its ability to cause vasoconstriction at higher concentrations, presumably due to its secondary effects on adrenergic receptors, and by its emetic effects due to peripheral D-2 stimulation. Agents selective for the peripheral D-1 receptors appear to offer significant advantages over treatments used currently for these and other related disorders (M. F. Lokhandwala, "Preclinical and Clinical Studies on the Cardiovascular and Renal Effects of Fenoldpam: A DA-1 Receptor Agonist", *Drug Development Research*, 113:123–124 (1987)).

Also, dopamine in combination with diuretics has been reported to reverse radio-contrast media-induced acute renal failure in patients (Talley et al., *Clin. Res.*, 18:518, 1970), thus suggesting that dopamine agonists may be similarly useful.

A wide variety of structures has been disclosed that are dopamine receptor ligands (H. E. Katerinopoulos and D. I. Schuster, "Structure-Activity Relationships for Dopamine Analogs: A Review", in *Drugs Of The Future*, Vol. 12, pp. 223–253, 1987) and include the thienopyridines, SKF 86926 (4-(3',4'-dihydroxyphenyl)-4,5,6,7-tetrahydrothieno(2,3-c)-pyridine) and SKF 86915 (7-(3', 4'-dihydroxyphenyl)-4,5,6, 7-tetrahydrothieno(3,2-c)-pyridine (P. H. Andersen et al., *European Journal of Pharmacology*, 137:291–292, 1987; and U.S. Pat. Nos. 4,340,600, to L. M. Brenner and J. R. Wardell, Jr., issued 1982, and 4,282,227, to L. M. Brenner, issued 1981). Nichols et al. have disclosed certain substituted trans-hexahydrobenzo[a]-phenanthridine compounds as dopaminergic ligands (D. E. Nichols and R. R. Mailman, U.S. Pat. No. 5,420,134, issued May 30, 1995; D. E. Nichols, U.S. Pat. No. 5,047,536, issued Sep. 10, 1991; W. K. Brewster et al., *Journal of Medicinal Chemistry*, 33:1756-1764, 1990; and D. E. Nichols and R. R. Mailman, PCT Application WO9324462, published Dec. 9, 1993).

Although various non-hydroxylated compounds having a fused four-ring system have been disclosed (see, for example, Kiguchi et al., *Heterocycles*, 19:1873–7, 1982; CA 98:16897, describing various intermediates to ergot alkaloids), it is pertinent to emphasize the structural requirements for dopaminergic activity. C. Kaiser and T. Jain, "Dopamine Receptors: Functions, Subtypes and Emerging Concepts", in *Medicinal Research Reviews*, Vol. 5, pp. 145–229, 1985), have discussed the structural requirements for dopamine activity and emphasized the important effect thereupon of the placement of hydroxyl groups in candidate compounds.

D. E. Nichols (U.S. Pat. No. 5,047,536, issued Sep. 10, 1991) disclosed that dihydrexidine is active as a dopamine agonist.

Michaelides et al., in PCT application WO94 22858 published Oct. 13, 1994, disclosed tetracyclic compounds of the formula:

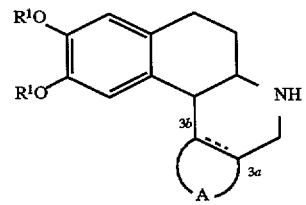

wherein A and the atoms to which it is attached and the optional double bond represent a mono- or di-heterocyclic ring selected from:

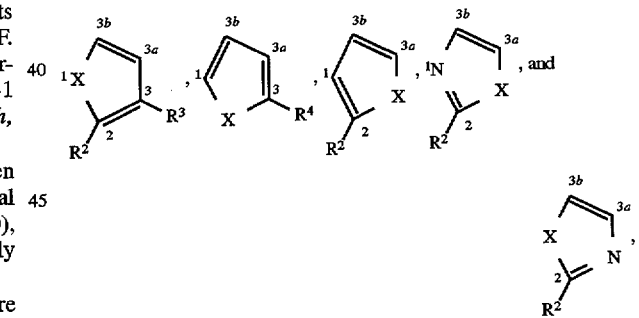

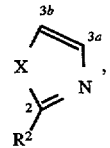

wherein X is sulfur or oxygen as having use in the treatment of dopamine-related neurological, psychological and cardiovascular disorders.

Applicants have now discovered that 2,6-, 3,6- and 4,6-diaza-5,6,6a,7,8,12b-hexahydrobenzo[c]phenanthrene compounds are useful agents for the treatment of dopamine-related neurological, psychological and cardiovascular disorders.

SUMMARY OF THE INVENTION

One aspect of the present invention is directed to dopamine agonists of the formula:

or pharmaceutically-acceptable salts, esters, carbamates or prodrugs thereof,
wherein:

$R^1$ is hydrogen or a readily-cleavable group;

A and the atoms to which it is attached comprise a pyridine ring selected from the group consisting of:

(a)

and (b)

wherein
one of X and Y is N and the other is $CR^2$, and $R^2$ and $R^3$ are independently selected from the group consisting of
hydrogen, Cl, Br, F, $C_1$–$C_6$-alkyl, $C_1$–$C_6$-alkoxy or $C_1$–$C_6$-haloalkyl; or additionally, one of $R^2$ and $R^3$ may be $C_3$–$C_7$-cycloalkyl; or when on adjacent carbon atoms $R^2$ and $R^3$ may be taken together with the atoms to which they are attached to form a $C_5$–$C_7$-cycloalkene ring.

The compounds of formula (I) have the ability to bind and activate dopamine receptors in the central and peripheral nervous systems, thus mimicking the activity of dopamine, and are therefore useful in the treatment of dopamine-related neurological, psychological and cardiovascular disorders, as well as in the treatment of substance abuse and other addictive behavior disorders, cognitive impairment and attention deficit disorder.

Accordingly, in a further aspect of the present invention are disclosed pharmaceutical compositions which are useful in the treatment of dopamine-related disorders, comprising a compound of the invention in combination with a pharmaceutically acceptable carrier.

In yet another aspect of the present invention is disclosed a method of treating dopamine-related disorders in human or animal patients in need of such treatment, comprising the administration to such patients of a therapeutically effective amount of a compound of the invention in amounts and for such a period of time as are sufficient to produce the desired result.

In still another aspect of the invention is disclosed a method for synthesizing the compounds claimed herein.

DETAILED DESCRIPTION OF THE INVENTION

In one embodiment of the invention are compounds of formula (I) wherein $R^1$ is as defined above and A and the atoms to which it is attached comprise a pyridine ring having the formula:

wherein one of X and Y is N and the other is $CR^2$, and $R^2$ and $R^3$ are independently selected from the group consisting of hydrogen, Cl, Br, F, $C_1$–$C_6$-alkyl, $C_1$–$C_6$-alkoxy or $C_1$–$C_6$-haloalkyl; or additionally, one of $R^2$ and $R^3$ may be $C_3$–$C_7$-cycloalkyl.

In another embodiment of the invention are compounds of formula (I) wherein $R^1$ is as defined above and A and the atoms to which it is attached comprise a pyridine ring having the formula:

wherein one of X and Y is N and the other is $CR^2$, and $R^2$ and $R^3$ are independently selected from the group consisting of hydrogen, Cl, Br, F, $C_1$–$C_6$-alkyl, $C_1$–$C_6$-alkoxy or $C_1$–$C_6$-haloalkyl; or additionally, one of $R^2$ and $R^3$ may be $C_3$–$C_7$-cycloalkyl.

In yet another embodiment of the invention are compounds of formula (I) wherein $R^1$ is as defined above and A and the atoms to which it is attached comprise a pyridine ring selected from the group consisting of:

wherein one of X and Y is N and the other is $CR^2$, and $R^2$ and $R^3$ are on adjacent carbon atoms and are taken together with the atoms to which they are attached to form a $C_5$–$C_7$-cycloalkene ring.

In a preferred embodiment of the invention are compounds of formula (I) wherein $R^1$ is as defined above and A and the atoms to which it is attached comprise a pyridine ring having the formula:

wherein $R^2$ and $R^3$ are independently selected from the group consisting of hydrogen, Cl, Br, F, $C_1$–$C_6$-alkyl, $C_1$–$C_6$-alkoxy or $C_1$–$C_6$-haloalkyl.

In a more preferred embodiment of the invention are compounds of formula (I) wherein $R^1$ is as defined above and A and the atoms to which it is attached comprise a pyridine ring having the formula:

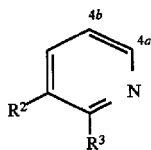

wherein R² is hydrogen and R³ is F or n-propyl.

Certain compounds of this invention may possess one or more asymmetric centers, including centers in a substituent group, such as an alkyl group, and may exist in optically-active forms. Pure d-isomers and pure l-isomers, racemic mixtures of the isomers, and mixtures thereof are intended to be within the scope of this invention. The stereochemistry at the fusion points (atoms 6a and 12b) of the saturated 6-membered rings in Formula (I), is preferably trans, although the absolute stereochemistry may be either (R) or (S), unless specifically noted otherwise. Chiral forms of certain compounds of this invention are contemplated and are specifically included within the scope of this invention.

The following are representative of the compounds of Formula (I):

trans-4,6-diaza-5,6,6a,7,8,12b-hexahydrobenzo[c]phenanthrene 10,11-diol;
trans-4,6-diaza-5,6,6a,7,8,12b-hexahydro-3-methylbenzo[c]phenanthrene 10,11-diol;
trans-4,6-diaza-5,6,6a,7,8,12b-hexahydro-3-propylbenzo[c]phenanthrene 10,11-diol;
trans-4,6-diaza-5,6,6a,7,8,12b-hexahydro-3-methoxybenzo[c]phenanthrene 10,11-diol;
trans-4,6-diaza-3-fluoro-5,6,6a,7,8,12b-hexahydrobenzo[c]phenanthrene 10,11-diol;
trans-4,6-diaza-5,6,6a,7,8,12b-hexahydrobenzo[c]phenanthrene 3,10,11-triol;
trans-4,6-diaza-5,6,6a,7,8,12b-hexahydro-2-methylbenzo[c]phenanthrene 10,11-diol;
trans-4,6-diaza-5,6,6a,7,8,12b-hexahydro-2-butylbenzo[c]phenanthrene 10,11-diol;
trans-4,6-diaza-5,6,6a,7,8,12b-hexahydro-2,3-dimethylbenzo[c]phenanthrene 10,11-diol;
trans-4,6-diaza-5,6,6a,7,8,12b-hexahydro-2,3-cyclohexenobenzo[c]phenanthrene 10,11-diol;
trans-2,6-diaza-5,6,6a,7,8,12b-hexahydrobenzo[c]phenanthrene 10,11-diol;
trans-2,6-diaza-4-fluoro-5,6,6a,7,8,12b-hexahydrobenzo[c]phenanthrene 10,11-diol;
trans-3,6-diaza-5,6,6a,7,8,12b-hexahydrobenzo[c]phenanthrene 10,11-diol;
trans-2,6-diaza-4-methyl-5,6,6a,7,8,12b-hexahydrobenzo[c]phenanthrene 10,11-diol;
trans-3,6-diaza-4-fluoro-5,6,6a,7,8,12b-hexahydro-2-methylbenzo[c]phenanthrene 10,11-diol; and
trans-3,6-diaza-4-chloro-5,6,6a,7,8,12b-hexahydro-2-methylbenzo[c]phenanthrene 10,11-diol;

or a pharmaceutically-acceptable salt, ester, carbamate or prodrug thereof.

The following are representative of the preferred compounds of Formula (I):

trans-4,6-diaza-5,6,6a,7,8,12b-hexahydrobenzo[c]phenanthrene 10,11-diol;
trans-4,6-diaza-5,6,6a,7,8,12b-hexahydro-3-methylbenzo[c]phenanthrene 10,11-diol;
trans-4,6-diaza-5,6,6a,7,8,12b-hexahydro-3-propylbenzo[c]phenanthrene 10,11-diol;
trans-4,6-diaza-5,6,6a,7,8,12b-hexahydro-3-methoxybenzo[c]phenanthrene 10,11-diol;
trans-4,6-diaza-3-fluoro-5,6,6a,7,8,12b-hexahydrobenzo[c]phenanthrene 10,11-diol;
trans-4,6-diaza-5,6,6a,7,8,12b-hexahydrobenzo[c]phenanthrene 3,10,11-triol;
trans-4,6-diaza-5,6,6a,7,8,12b-hexahydro-2-methylbenzo[c]phenanthrene 10,11-diol;
trans-4,6-diaza-5,6,6a,7,8,12b-hexahydro-2-butylbenzo[c]phenanthrene 10,11-diol;
trans-4,6-diaza-5,6,6a,7,8,12b-hexahydro-2,3-dimethylbenzo[c]phenanthrene 10,11-diol; and
trans-4,6-diaza-5,6,6a,7,8,12b-hexahydro-2,3-cyclohexenobenzo[c]phenanthrene 10,11-diol;

or a pharmaceutically-acceptable salt, ester, carbamate or prodrug thereof.

The following are representative of the more preferred compounds of Formula (I):

trans-4,6-diaza-5,6,6a,7,8,12b-hexahydro-3-propylbenzo[c]phenanthrene 10,11-diol; and
trans-4,6-diaza-3-fluoro-5,6,6a,7,8,12b-hexahydrobenzo[c]phenanthrene 10,11-diol;

or a pharmaceutically-acceptable salt, ester, carbamate or prodrug thereof.

One object of the present invention is to provide a process for the preparation of a compound having the formula

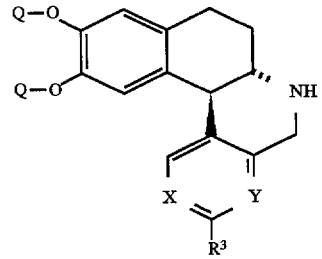

wherein $R^1$ is hydrogen or a readily-cleavable group and one of X and Y is N and the other is $R^2$, wherein $R^2$ and $R^3$ are independently selected from the group consisting of hydrogen, Cl, Br, F, $C_1$–$C_6$-alkyl, $C_1$–$C_6$-alkoxy or $C_1$–$C_6$-haloalkyl; the method comprising reacting a compound having the formula

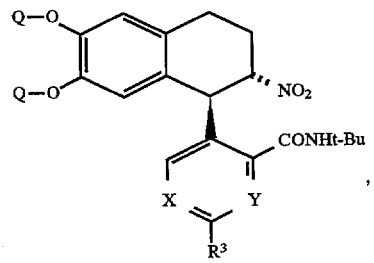

wherein Q, X, Y, $R^2$ and $R^3$ are as above with an excess of zinc dust and aqueous HCl, and isolating the product compound.

Another object of the present invention is to provide a process for the preparation of trans-diaza-5,6,6a,7,8,12b-hexahydro-benzo[c]phenanthrene 10,11-diols having the Formula (Ia)

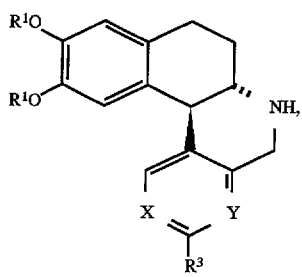

(Ia)

wherein X, Y, $R^1$, $R^2$ and $R^3$ are as above; by means of a series of steps one of which is the process described above, the method comprising:

(a) treating a compound having the formula

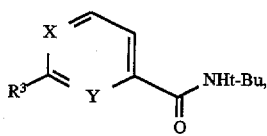

wherein X, Y, $R^2$ and $R^3$ are as defined above, with two equivalents of a strong base, such as, for example n-butyllithium or t-butyllithium or a similar alkyl-lithium reagent at $-78°$ C. for 30 minutes, followed by reaction with a compound having the formula

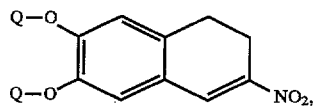

wherein Q is a protecting group selected from an ether moiety, an alkoxyalkyl ether moiety, an alkylthioalkyl ether moiety, a trialkylsilyl ether moiety, or a cyclic acetal or ketal moiety; followed by treatment of the reaction mixture with a weak base in a solvent such as methanol, ethanol or acetonitrile, for example, and isolating the product compound having the formula (a1)

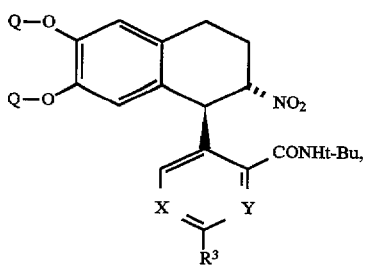

(a1), wherein Q, X, Y, $R^2$ and $R^3$ are as above;

(b) reacting compound (a 1) with an excess of zinc dust and HCl, and isolating the product compound having the formula (b 1)

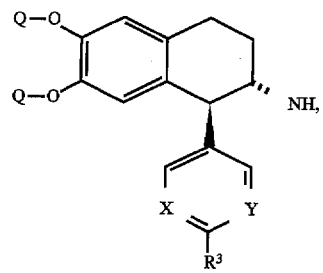

(b1), wherein Q, X, Y, $R^2$ and $R^3$ are as above;

(c) deprotecting compound (b1) by treatment with $BBr_3$ in a chlorinated solvent, such as methylene chloride, chloroform or carbon tetrachloride, or the like, at $-78°$ C. to room temperature and isolating the product (Ia) wherein $R^1$ is hydrogen and X, Y, $R^2$ and $R^3$ are as above; and isolating the product (Ia).

In the process shown above, an optional step may be appended wherein the grouping wherein $R^1$=hydrogen of the product (Ia) of step (c) is replaced with a readily-cleavable group, as defined below, by reaction with a suitable reagent, and isolating the product (Ia) wherein $R^1$ is a readily-cleavable group.

In step (a) of the above process the ether moiety may be, for example, an alkyl, alkenyl, or cycloalkyl ether such as methyl, isopropyl, t-butyl, cyclopropylmethyl, cyclohexyl and allyl; the alkoxyalkyl ether moiety may be, for example, methoxymethyl or methoxyethoxymethyl or the like; the alkylthioalkyl ether moiety may be, for example, methylthiomethyl; tetrahydropyranyl or arylalkyl such as benzyl, o-nitrobenzyl, 9-anthrylmethyl, 4-picolyl or the like; the trialkylsilyl ether moiety may be, for example, trimethylsilyl, triethylsilyl, t-butyldimethylsilyl, or the like; and the cyclic acetal or ketal moiety may be, for example, methylene acetal, acetonide, cyclohexylidene ketal, diphenylmethylene ketal, or the like. Also, the weak base may be, for example, triethylamine, diisopropylethylamine, or 1,8-diazabicyclo[5.4.0]undec-7-ene (DBU).

Another object of the present invention is to provide an alternate process for the preparation of trans-diaza-5,6,6a,7,8,12b-hexahydro-benzo[c]phenanthrene 10,11-diols having the Formula (Ib)

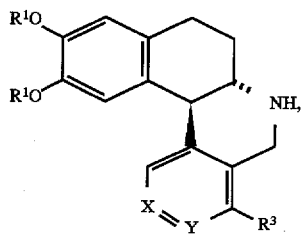

(Ib)

wherein $R^1$ is hydrogen or a readily-cleavable group, one of X and Y is N and the other is $CR^2$, wherein $R^2$ and $R^3$ are independently selected from the group consisting of hydrogen, Cl, Br, F, $C_1$–$C_6$-alkyl, $C_1$–$C_6$-alkoxy or $C_1$–$C_6$-haloalkyl;

the method comprising:

(a) treating a compound having the formula

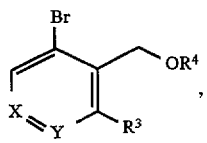

wherein X=N and Y=CR² or Y=N and X=CR², R² and R³ are as defined above, and R⁴ is a protecting group, with a strong base at −78° C. for 10 minutes, followed by reaction with a compound having the formula

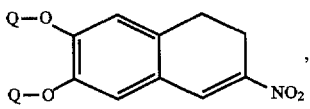

wherein Q is a protecting group selected from an ether moiety, an alkoxyalkyl ether moiety, an alkylthioalkyl ether moiety, a trialkylsilyl ether moiety, or a cyclic acetal or ketal moiety; followed by treatment of the reaction mixture with a weak base in a solvent such as methanol, ethanol or acetonitrile, for example, and isolating the product compound having the formula (a2)

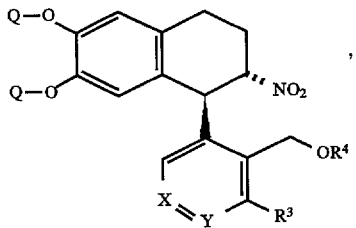

wherein Q, X, Y, R², R³ and R⁴ are as above;

(b) removing the R4 grouping from compound (a2) by treatment with a suitable reagent, such as HCl, for example, when R⁴ is THP or MOM, or hydrogenolysis with Pd/C when R⁴ is benzyl, followed by reducing the nitro group with zinc dust and a strong acid, protecting the newly formed amine by reaction with di-t-butyl-dicarbonate and isolating the product compound having the formula (b2)

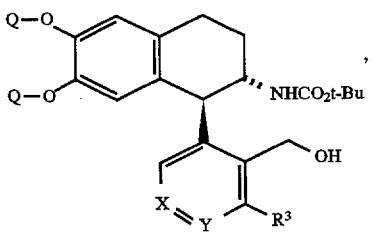

wherein Q, X, Y, R² and R³ are as above;

(c) treating compound (b2) with methanesulfonyl chloride in TEA to convert the hydroxyl group to a methanesulfonyl group, reacting the methanesulfonyl group with LiCl in DMF to replace the methanesulfonyl group with a chlorine atom, then deprotecting the protected-amino group of this compound by treatment with HCl, and cyclizing the deprotected compound by treatment with K₂CO₃ in t-butanol at reflux to give the compound (b3)

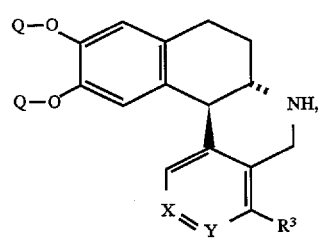

(d) deprotecting compound (b3) by treatment with BBr3 in a chlorinated solvent such as methylene chloride, chloroform or carbon tetrachloride, or the like, at −78° C. to room temperature and isolating the product (Ib) wherein R¹ is hydrogen and X, Y, R² and R³ are as above.

In the process shown above, an optional step may be appended wherein the grouping wherein R¹=hydrogen of the product (Ib) of step (d) is replaced with a readily-cleavable group, as defined below, by reaction with a suitable reagent, and isolating the product (Ib) wherein R¹ is a readily-cleavable group.

In step (a) of the above process the protecting group may be, for example, methoxymethyl (MOM), tetrahydropyranyl (THP) or benzyl, and strong base may be, for example n-butyllithium or t-butyllithium or a similar alkyllithium reagent. Also in step (a) of the above process the ether moiety may be, for example, an alkyl, alkenyl, or cycloalkyl ether such as methyl, isopropyl, t-butyl, cyclopropylmethyl, cyclohexyl and allyl; the alkoxyalkyl ether moiety may be, for example, methoxymethyl or methoxyethoxymethyl or the like; the alkylthioalkyl ether moiety may be, for example, methylthiomethyl; tetrahydropyranyl or arylalkyl such as benzyl, o-nitrobenzyl, 9-anthrylmethyl, 4-picolyl or the like; the trialkylsilyl ether moiety may be, for example, trimethylsilyl, triethylsilyl, t-butyldimethylsilyl, or the like; and the cyclic acetal or ketal moiety may be, for example, methylene acetal, acetonide, cyclohexylidene ketal, diphenylmethylene ketal, or the like. Also, the weak base may be, for example, triethylamine, diisopropylethylamine, or 1,8-diazabicyclo[5.4.0]undec-7-ene (DBU).

"$C_1$–$C_6$-alkyl" means a straight- or branched-chain hydrocarbon radical containing from one-to-six carbon atoms, including as appropriate, for example, methyl, ethyl, n-propyl, i-propyl, n-butyl, sec-butyl, i-butyl, t-butyl, pentyl, hexyl, and the like.

"$C_1$–$C_6$-alkoxy" means a straight- or branched-chain hydrocarbon radical having one-to-six carbon atoms which is joined to the rest of the molecule via an ether linkage (i.e., through an oxygen atom), for example, methoxy, ethoxy, i-propoxy, t-butoxy, 3-pentoxy, hexoxy, and the like.

"$C_3$–$C_7$-cycloalkyl" or "$C_3$–$C_5$-cycloalkyl" means a cyclic hydrocarbon ring containing from three-to-seven carbon atoms or from three-to-five carbon atoms, respectively, including, for example, as appropriate, cyclopropyl, cyclobutyl, cyclopentyl, cyclohexyl or cycloheptyl.

$C_1$–$C_6$-haloalkyl means a $C_1$–$C_6$-alkyl radical, as defined, above, substituted with from one to three halogen atoms selected from chlorine, bromine and fluorine, including for example, 6-chlorohexyl, 5-bromopentyl, trifluoromethyl, trichloroethyl, fluoropropyl, bromobutyl, and the like.

"$C_5$–$C_7$-cycloalkene" means a singly unsaturated cyclic hydrocarbon radical having five-to-seven carbon atoms, wherein the unsaturation occurs at the points of attachment to the fused ring, including for example, cyclopentene, cyclohexene, and cycloheptene.

"Readily-cleavable group", as used herein, means substituents which are readily cleaved under physiological conditions, for example, by hydrolysis in blood or tissue in vivo, to yield the compound of Formula (I) wherein $R^1$ is hydrogen. Readily-cleavable groups include those substituents commonly referred to as "prodrug moieties", see, e.g., T. Higuchi and V. Stella who provide a thorough discussion of the prodrug concept in *Pro-drugs as Novel Delivery Systems*, Vol. 14 of the A.C.S. Symposium Series, American Chemical Society (1975). Examples of readily-cleavable groups include, but are not limited to, acetyl, trimethylacetyl, butanoyl, methyl succinoyl, t-butyl succinoyl, ethoxycarbonyl, methoxycarbonyl, benzoyl, 3-aminocyclohexylidenyl, and the like. Such compounds are prepared by reaction with a reagent capable of adding a readily-cleavable group, such as for example, acetic anhydride, trimethylacetyl chloride, butanoic anhydride, methyl succinoyl chloride, t-butyl succinoyl chloride, diethyldicarbonate, dimethyldicarbonate, benzoyl chloride, or 3-aminocyclohexanone, and the like.

"Pharmaceutically-acceptable salts, esters, carbamates and prodrugs" refers, respectively, to those salts, esters, carbamates and prodrugs which are, within the scope of sound medical judgment, suitable for use in contact with the tissues of humans and lower animals without undue toxicity, irritation, allergic response and the like, and are commensurate with a reasonable benefit/risk ratio, effective for their intended use in the treatment of psychological, neurological, cardiovascular and addictive behavior disorders.

Pharmaceutically-acceptable salts are well known in the art, as exemplified, for example, by S. M. Berge et al., who describe pharmaceutically-acceptable salts in detail in *J. Pharm. Sci.*, 66:1-19, 1977. The salts may be prepared in situ during the final isolation and purification of the compounds of Formula (I), or separately by reacting the free base function with a suitable organic acid. Representative acid-addition salts include hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts, and the like. Representative alkali or alkaline earth metal salts include sodium, calcium, potassium, magnesium salts, and the like.

Pharmaceutically-acceptable ester groups include those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, for example, formates, acetates, propionates, butyrates, acrylates and ethylsuccinates. Examples of prodrug ester groups include pivoyloxymethyl, acetoxymethyl, phthalidyl, indanyl and methoxymethyl, as well as other such groups known in the art.

Examples of pharmaceutically-acceptable, nontoxic carbamates of the compounds of Formula I include carbamates derived from the phenolic groups (R'NHCO-phenol) or the ring nitrogen atom ring (—N—CO—O—R") wherein R' and R" may be $C_1$–$C_6$-alkyl groups, which may be straight- or branched-chain, or aromatic groups or heterocyclic residues. Carbamates of the compounds of Formula I may be prepared according to conventional methods.

The term "prodrug" refers to compounds that are rapidly transformed under physiological conditions to yield the parent compounds of Formula (I), as for example, by hydrolysis in blood in vivo. T. Higuchi and V. Stella provide a thorough discussion of the prodrug concept in *Prodrugs as Novel Delivery Systems*, Vol. 14 of the A.C.S. Symposium Series, American Chemical Society (1975). Examples of prodrugs for compounds containing hydroxy groups may be found in *Bioreversible Carriers in Drug Design: Theory and Application*, edited by E. B. Roche, Pergamon Press (1987).

The term "administration" of the dopaminergic agent or composition, as used herein, refers to systemic use, as when taken orally, parenterally, by inhalation spray, by nasal, rectal or buccal routes, or topically in dosage form unit formulations containing conventional nontoxic pharmaceutically-acceptable carriers, adjuvants and vehicles, as desired.

The term "parenteral", as used herein, includes intravenous, intramuscular, intraperitoneal, intrasternal, subcutaneous and intraarticular injection and infusion techniques.

As used herein, the term "pharmaceutically-acceptable carriers" means a non-toxic, inert solid, semi-solid or liquid filler, diluent, encapsulating material or formulation auxiliary of any type. Some examples of the materials that can serve as pharmaceutically-acceptable carriers are sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants, such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically-acceptable antioxidants include water-soluble antioxidants, such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alpha-tocopherol and the like; and the metal chelating agents, such as citric acid, ethylenediamine tetraacetic acid (EDTA), sorbitol, tartaric acid, phosphoric acid and the like.

By a "therapeutically-effective amount" of a dopaminergic agent is meant a sufficient amount of the compound to treat dopamine-related disorders at a reasonable benefit/risk ratio applicable to any medical treatment. It will be understood, however, that the total daily usage of the compounds and compositions of the present invention will be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient; the time of administration, route of administration, and rate of excretion of the specific compound employed; the duration of the treatment; drugs used in combination or coincidentally with the specific compound employed; and like factors well known in the medical arts.

The term "affective disorder" as used herein refers to disorders that are characterized by changes in mood as the primary clinical manifestation, for example, depression.

The term "antipsychotic agent", as used herein, refers to drugs used extensively in the symptomatic management of all forms of schizophrenia, organic psychosis, the manic phase of manic depressive illness and other acute idiopathic illnesses, and occasionally used in the treatment of depression or in severe anxiety.

The term "attention deficit disorder" refers to a recently-classified pediatric neuropsychiatric disorder characterized by inattention, impulsivity, distractibility and sometimes hyperactivity, which replaces the less formal diagnoses of hyperactivity syndrome, hyperkinetic syndrome, minimal brain dysfunction and specific learning disability. The disorder is prevalent among pre-adolescent children and is reflected in poor school performance and social behavior and has been described in experimental reports of impaired perceptual, cognitive and motor function.

The term "cognitive impairment" refers to a deficiency in any of the aspects of the cognitive (information processing) functions of perceiving, thinking and remembering.

The term "dopamine-related cardiovascular disorders", as used herein, refers to conditions which can be reversed or improved by administration of dopamine or a dopaminergic agent, either alone or in combination therapy with other classes of cardiovascular agents. The usefulness of dopaminergic agents in cardiovascular diseases, for example in the treatment of shock and congestive heart failure, is based on the known, but incompletely understood, role of dopamine in the cardiovascular system, especially the effects of dopamine on the heart and the ability of dopamine to produce vasoconstriction while maintaining blood flow through renal and mesenteric beds. Also included are other related, potential uses for dopaminergic agents which include, for example, use in renal failure.

The term "dopamine-related neurological and psychological disorders", as used herein, refers to behavioral disorders, such as psychoses and addictive behavior disorders; affective disorders, such as major depression; and movement disorders, such as Parkinson's disease, Huntington's disease and Gilles de la Tourette's syndrome; which have been linked, pharmacologically and/or clinically, to either insufficient or excessive functional dopaminergic activity in the CNS. Also included are miscellaneous indications for which dopaminergic agents have been found to be clinically useful. Examples of such indications include disorders characterized by vomiting, such as uremia, gastroenteritis, carcinomatosis, radiation sickness, and emesis caused by a variety of drugs, intractable hiccough and alcoholic hallucinosis. "Normal dopamine levels" are those levels of dopamine that are found in the brains of control subjects and are usually measured as levels of the dopamine metabolites homovanillic acid (3-methoxy-4-hydroxyphenylacetic acid) and 3,4-dihydroxyphenylacetic acid. Abnormal dopamine levels are those levels that are not within the range of dopamine levels found in the brains of control subjects.

The term "substance abuse", as used herein, refers to periodic or regular self-administration of psychoactive substances in the absence of medical indications and despite the presence of persistent or recurrent social, occupational, psychological or physical problems that the person knows are caused by or may be exacerbated by continued use of the substance.

This invention also provides pharmaceutical compositions in unit dosage forms, comprising a therapeutically-effective amount of a compound (or compounds) of this invention in combination with a conventional pharmaceutical carrier.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally-acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil may be employed, including synthetic mono- or diglycerides. Also, fatty acids, such as oleic acid, are used in the preparation of injectables.

The injectable formulation may be sterilized, for example, by filtration through a bacteria-retaining filter, or by incorporating sterilizing agents in the form of sterile solid compositions which may be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of the drug in a crystalline or amorphous material which has poor water solubility The rate of absorption of the drug becomes dependent on the rate of dissolution of the drug which is, in turn, dependent on the physical state of the drug, for example, the crystal size of the drug and its crystalline form. Another approach to delaying absorption of a drug is to administer the drug as a solution or suspension in oil. Injectable depot forms may also be made by forming microcapsule matrices of drugs and biodegradable polymers, such as with polylactide-polyglycolide. Depending on the ratio of drug to polymer and the composition of the polymer, the rate of drug release may be controlled by this method. Examples of other biodegradable polymers include polyorthoesters and polyanhydrides. The depot injectables can also be made by entrapping the drug in liposomes or microemulsions which are compatible with body tissues.

Suppositories for rectal administration of the drug may be prepared by mixing the drug with a suitable non-irritating excipient, such as cocoa butter and polyethylene glycol, both of which are solid at ordinary temperature, but liquid at the rectal temperature and will therefore melt in the rectum, releasing the drug.

Solid dosage forms for oral administration may include capsules, dragees, granules, pills, powders, prills and tablets. In such solid dosage forms the active compound may be admixed with at least one inert diluent, such as sucrose, lactose or starch, such dosage forms may also comprise, as is normal practice, additional substances other than inert diluents, e.g., tableting lubricants and other tableting aids, such as magnesium stearate and microcrystalline cellulose. In the case of capsules, tablets and pills, the dosage forms may also comprise buffering agents. Tablets and pills may additionally be prepared with enteric coatings and other release-controlling coatings.

Solid compositions of a similar type may also be employed as fillers in soft and hard-filled gelatin capsules using such excipients as lactose or milk sugar, as well as high molecular weight polyethylene glycols and the like.

Liquid dosage forms for oral administration may include pharmaceutically-acceptable emulsions, microemulsions, solutions, suspensions, syrups and elixirs containing inert diluents commonly used in the art, such as water, and may also comprise adjuvants, such as wetting agents; emulsifying and suspending agents; sweetening, flavoring and perfuming agents.

If desired, the compounds of the present invention can be incorporated into slow release or targeted-delivery systems, such as polymer matrices, liposomes and microspheres.

The active compounds may also be in micro-encapsulated form with one or more excipients, as noted above. The solid dosage forms of capsules, dragees, granules, pills, and tablets may be prepared with coatings and shells, such as enteric coatings and other coatings well-known in the pharmaceutical formulating art. They may optionally contain opacifying agents, and may also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or transdermal patches. The active component is admixed under sterile conditions with a pharmaceutically-acceptable carrier and any needed preservatives or buffers, as required. Ophthalmic formulations, ear drops, eye ointments, powders and solutions are also contemplated as being within the scope of this invention. Administration sublingually, from one or more of the above dosage forms, is also contemplated as a suitable mode of administration of the compounds of the invention.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to the compounds of this invention, excipients, such as lactose, talc, silicic acid, aluminum hydroxide, calcium silicates and polyamide powder, or mixtures of these substances. Sprays may additionally contain customary propellants, such as chlorofluorohydrocarbons or environmentally- and pharmaceutically-acceptable substitutes.

Transdermal patches have the added advantage of providing controlled delivery of a compound to the body. Such dosage forms may be made by dissolving or dispersing the compound in the proper medium. Absorption enhancers may also be used to increase the flux of the compound across the skin. The rate may be controlled by either providing a rate-controlling membrane or by dispersing the compound in a polymer matrix or gel.

The total daily dose of the compounds of this invention administered to a host in single or in divided doses may be in amounts, for example, from 0.01 to 50 mg/kg body weight or more, usually from 0.1 to 30 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in multiple doses or in a single dose.

The compounds of the present invention may be administered alone or in combination or in concurrent therapy with other agents which effect the dopaminergic system, for example, L-dopa, amantadine, apomorphine or bromocryptine; and with cholinergic agents, for example, benztropine, biperiden, ethopromazine, procyclidine, trihexylphenidyl, and the like. The compounds of the present invention may also be co-administered with agents, for example, enzyme inhibitors, which block their metabolic transformation outside the CNS.

Synthetic methods

In general, the compounds of this invention are synthesized by reaction schemes 1 and 2 as illustrated below. It should be understood that $R^1$–$R^3$, as used herein, correspond to these like-numbered R groups identified by Formula (I). The oxygen atoms of the catechol groups may be derivatized with protecting groups (Q), which are known in the art and may be prepared by conventional methods. These derivatizing groups may be selected from among phenol derivatives and derivatives which are suitable to catechols because of the proximity of the two hydroxyl functions. Commonly-used phenol derivatives are, for example an alkyl, alkenyl, and cycloalkyl ether moiety, for example, methyl, isopropyl, t-butyl, cyclopropylmethyl, cyclohexyl and allyl; an alkoxyalkyl ether moiety, such as methoxymethyl or methoxyethoxymethyl and the like; an alkylthioalkyl ether moiety, such as methylthiomethyl; tetrahydropyranyl, arylalkyl, such as benzyl, o-nitrobenzyl, 9-anthrylmethyl, 4-picolyl and the like; a trialkylsilyl ether moiety, such as trimethylsilyl, triethylsilyl, t-butyldimethylsilyl, and the like; or a cyclic acetal or ketal moiety, such as methylene acetal, acetonide, cyclohexylidene ketal, diphenylmethylene ketal, and the like;

In accordance with Scheme 1, compounds (1) or (2) may be converted to their respective dianions by treatment with a strong base, such as for example n-butyllithium or t-butyllithium, or a similar alkyllithium reagent, at −78° C. The dianions are subsequently reacted with compound (3) then treated with a weak base, such as triethylamine, diisopropyethylamine, and 1,8-diazabicyclo[5.4.0]undec-7-ene (DBU), for example in a solvent such as methanol, ethanol or acetonitrile, for example, to provide the compounds (4) and (5), respectively. Compounds (4) and (5) may then be reduced with zinc dust and a strong acid, such as HCl, to give compounds (6) and (7). Treating compounds (6) and (7) with an acid such as p-toluenesulfonic acid in a refluxing solvent such as toluene, benzene, xylene or the like, provides an intermediate lactam which is reduced by a reducing agent such as $BH_3$·THF or LAH in THF or ether to give compounds (8) and (9), respectively. Alternately, compounds (4) and (5) may be treated with an excess of zinc dust and a strong acid, such as HCl, to prepare the compounds (8) and (9) directly. Deprotection of the compounds (8) and (9) may be accomplished with a reagent such as $BBr_3$ in a chlorinated solvent such as methylene chloride, chloroform or carbon tetrachloride, or the like, at −78° C. to room temperature in order to provide the compounds (10) and (11 ), respectively. Alternately, after the protecting groups have been removed from compounds (8) and (9), they may be replaced with readily-cleavable groups, $R^1$, as defined above, by reaction with a suitable reagent selected from those described by Higuchi & Stella (op. cit.).

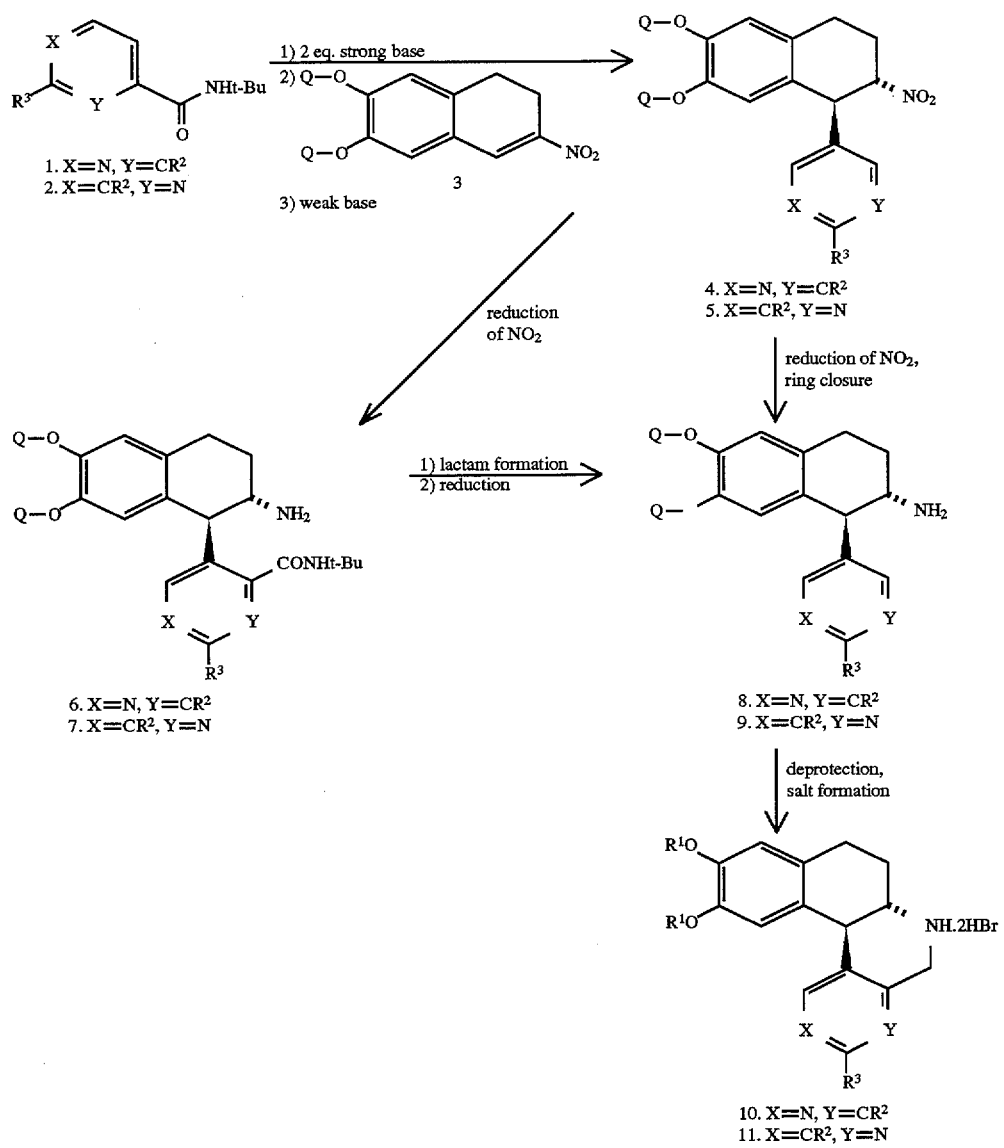

Scheme 2

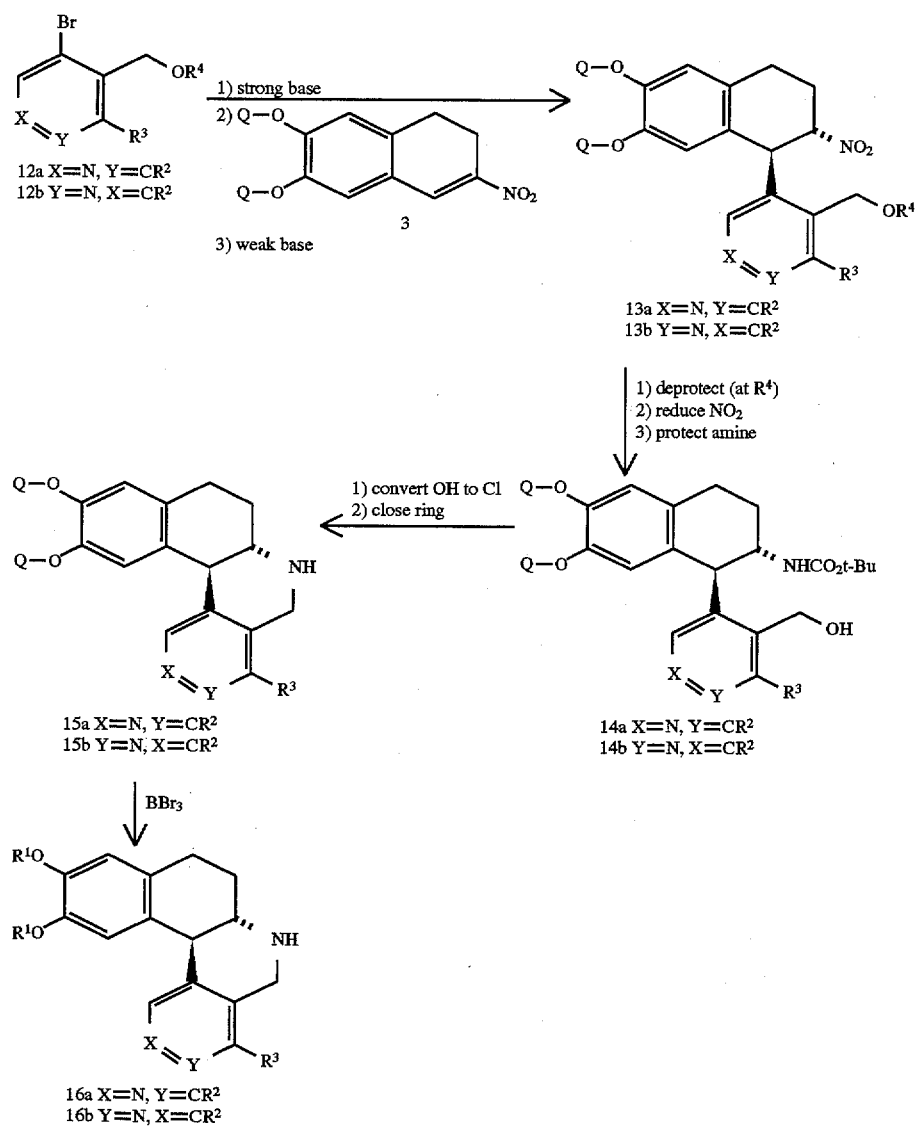

In accordance with Scheme 2, compounds of formula (12) wherein X, Y, $R^2$ and $R^3$ are as defined in Formula (I) above and $R^4$ is a protecting group such as methoxymethyl (MOM), tetrahydropyranyl (THP) or benzyl may be converted to anions by halogen-metal exchange with, for example, n-butyllithium or t-butyllithium at −78° C. The anions are subsequently reacted with compound (3) then treated with a weak base, such as triethylamine in a solvent such as methanol, for example, to provide the compounds (13), respectively. Compounds (13) may then be deprotected by a suitable reagent, such as HCl, for example, when $R^4$ is THP or MOM, or hydrogenolysis with Pd/C when $R^4$ is benzyl, then the nitro group is reduced with zinc dust and a strong acid, and the newly formed amine is protected with a suitable protecting group, such as a carbamate, by reaction with di-t-butyl-dicarbonate, for example, to give the compounds (14). The hydroxyl group of compounds (14) is converted to the corresponding halide, for example the chloride, by any of several standard literature methods, for example, by treatment with methanesulfonyl chloride in TEA followed by reaction of the intermediate with LiCl in DMF. The protected amino group of the intermediate halide compound is then deprotected with an acid such as HCl, and the deprotected intermediate is cyclized by treatment with a base such as $K_2CO_3$ in a solvent such as t-butanol at reflux, for example, to give compounds (15). Conversion of compounds (15) to compounds (16) wherein $R^1$ is hydrogen is accomplished with a reagent such as $BBr_3$ in a chlorinated solvent such as methylene chloride, chloroform or carbon tetrachloride, or the like, at −78° C. to room temperature. Alternately, after the protecting groups have been removed from compounds (15), they may be replaced with readily-removable groups, $R^1$, as defined above, by reaction with a suitable reagent selected from those described by Higuchi & Stella (op. cit.).

Starting material compounds (1) and (2) may be obtained from commercial suppliers, or prepared from the appropriate pyridine carboxylic acids, which in turn may be commercially available or prepared by standard reactions such as carboxylation or lithiation and nucleophilic reactions commonly used by those skilled in the art. Compound (12a) may be obtained from commercial suppliers or prepared from 2,6-substituted-4-bromopyridine compounds by standard lithiation and nucleophilic reactions commonly used by those skilled in the art. Compounds (12b) may be obtained from commercial suppliers or prepared according to the procedures described by Gu and Bayburt, Tetrahedron Letters, 1996, in press.

Certain abbreviations are used above and within the experimental section of this application. They are: DIBAL for diisobutylaluminum hydride; DBU for 1,8-diazabicyclo [5.4.0]undec-7-ene; DMF for dimethyl formamide; DMSO for dimethyl sulfoxide; LAH for lithium aluminum hydride; LDA for lithium diisopropylamide; MOM for methoxymethyl; PPTS for pyridinium p-toluenesulfonate; THF for tetrahydrofuran; and THP for tetrahydropyranyl.

The foregoing may be better understood by reference to the following examples which are provided for the illustration and not limitation of the invention.

EXAMPLE 1 trans-4,6-diaza-5,6,6a,7,8,12b-hexahydrobenzo[c] phenanthrene 10,11-diol dihydrobromide 1a. picolinic acid t-butylamide To a cooled solution of picolinic acid (3.6 g, 29.2 mmole, Aldrich) and triethylamine (8 mL, 57.4 mmole) in 80 mL of methylene chloride at 0° C. was added pivaloyl chloride (3.8 mL, 30.8 mmole). The mixture was stirred for 1 hour at 0° C., t-butylamine (4.0 mL, 38.1 mmole) was added, and stirring was continued for 1 hour at 0° C. and 1 hour at room temperature. Saturated $NaHCO_3$ (30 mL) was added, the layers were separated, and the aqueous layer was extracted with methylene chloride (2×30 mL). The combined organic solutions were dried and concentrated, and the residue was chromatographed in silica gel, eluting with 30 to 60% ethyl acetate in hexane, to provide 5.2 g of the title compound as an oil. MS: 179 $(M+H)^+$; $^1H$ NMR $(CDCl_3)$ δ: 8.52 (m, (1H), 8.18 (dm, J=7.5 Hz, 1H), 8.0 (s, br, 1H), 7.84 (dt, J=7.5, 1.5 Hz, 1H), 7.40 (ddd, J=7.5, 5.0, 1.5 Hz, 1H), 1.50 (s, 9H).

1b. trans-1,2,3,4-tetrahydro-6,7-dimethoxy-1-(2-t-butylcarboxyamido-3-pyridyl)-2-nitronaphthalene A sample of picolinic acid t-butylamide (1.026 g, 5.76 mmole, from step 1a) was dissolved in 50 mL of THF, the solution was cooled to −78° C., and n-butyllithium (11.75 mmole) was added dropwise. The reaction mixture was stirred for 30 minutes at −78° C., a solution of 1,2-dihydro-6,7-dimethoxy-3-nitronaphthalene (5.43 mmole, prepared as described in PCT application WO9422858, published Oct. 13, 1994) in 25 mL of THF, cooled to −78° C. was added via cannula, and the mixture was stirred for 2 hours at −78° C. Saturated $NH_4Cl$ (20 mL) was added, the mixture was allowed to warm to room temperature, and the layers were separated. The aqueous layer was extracted with methylene chloride (4×30 mL). The combined organic solution was dried and concentrated. The residue was dissolved in 20 mL of methanol then 2 mL of triethylamine was added, and the solution was stirred at room temperature for 16 hours. The solvent was removed, and the residue was chromatographed on silica gel, eluting with 20 to 50% ethyl acetate in hexane, to provide 1.23 g of the title compounds as a solid (55%). MS: 414 $(M+H)^+$, 431 $(M+NH_4)^+$; $^1H$ NMR $(CD_3OD)$ δ: 8.45 (m, 1H), 8.13 (br s, 1H), 7.49–7.39 (m, 2H), 6.75 (s, 1H), 6.36 (s, 1H), 5.55 (d, J=6 Hz, 1H), 5.21 (m, 1H), 3.81 (s, 3H), 3.59 (s, 3H), 3.07–2.96 (m, 1H), 2.87–2.76 (m, 1H), 2.47–2.27 (m, 2H), 1.42 (s, 9H).

1c. trans-4,6-diaza-5,6,6a,7,8,12b -hexahydro-10,11-dimethoxybenzo[c]phenanthrene To a solution of the compound from step 1b above (2.95 mmole) in 40 mL of ethanol was added 6N HCl (6 mL). Zn dust was added in portions until the reaction was complete (as shown by TLC); a large excess (>30 equivalents) of zinc dust was needed.

The mixture was made basic by addition of saturated $NaHCO_3$. NaCl (50 g) was added, the mixture stirred vigorously for 20 minutes, and the solids were removed by filtration. The filtrate was extracted with methylene chloride (4×50 mL), the organic extract was dried $(MgSO_4)$ and concentrated, and the residue was purified by preparative TLC to afford 200 mg of the title compound. MS: 297 $(M+H)^+$; $^1H$ NMR $(CDCl_3)$δ:8.48 (d, J=4.5 Hz, 1H), 7.82 (d, J=7.5 Hz, 1H), 7.22 (dd, J=7.5 and 4.5 Hz, 1H), 6.77 (s, 1H), 6.73 (s, 1H), 4.22 (m, 2H), 3.89 (s, 3H), 3.88 (m, 1H), 3.78 (s, 3H), 3.02–2.72 (m, 3H), 2.21 (m, 1H), 1.75 (m, 1H).

1d. trans-4,6-diaza-5,6,6a,7,8,12b-hexahydrobenzo[c] phenanthrene 10,11-diol dihydrobromide To a solution of the compound from step 1c above (0.328 mmole) in 15 mL of methylene chloride cooled to −78° C. was added $BBr_3$ (2.0 mmole). The resulting suspension was stirred at −78° C. for 30 minutes and then warmed to 0° C., The stirring was continued for 30 minutes at 0° C. and for 4 hours at room temperature. The mixture was recooled to −78° C., and methanol (4 mL) was added. The cooling bath was removed, and the resulting solution was stirred for 45 minutes at room temperature. The solvent was removed, and the residue was dried under vacuum to provide 150 mg of the title compound. MS: 269 $(M+H)^+$; $^1H$ NMR $(CD_3OD)$ δ: 8.74 (d, J=5 Hz, 1H), 8.46 (d, J=8 Hz, 1H), 7.86 (dd, J=8 and 5 Hz, 1H), 6.72 (s, 1H), 6.70 (s, 1H), 4.76 (s, 2H), 4.42 (d, J=11 Hz, 1H), 3.35 (m, 1H), 3.30–2.79 (m, 2H), 2.38 (m, 1H), 2.10–1.96 (m, 1H). Anal. Calcd. for $C_{16}H_{16}N_2O_2 \cdot 2.5$ HBr·0.60 $H_2O$: C, 39.92; H, 4.13; N, 5.82; Found: C, 39.96; H, 4.19; N, 5.02.

EXAMPLE 2 trans-4,6-diaza-5,6,6a,7,8,12b-hexahydro-3-methylbenzo[c]phenanthrene 10,11-diol dihydrobromide Following the procedures of Example 1, except substituting 6-methyl-2-pyridinecarboxylic acid (TCI America Organic Chemicals) for the picolinic acid of step 1a, and carrying the product forward as in steps 1a–1d, the title compound was prepared. MS: 283 $(M+H)^+$; $^1H$ NMR $(CD_3OD)$ δ: 8.51 (d, J=8 Hz, 1H), 7.85 (d, J=8 Hz, 1H), 6.72 (s, 1H), 6.67 (s, 1H), 4.79 (m, 2H), 4.42 (d, J=11 Hz, 1H), 3.37 (m, 1H), 3.01–2.84 (m, 2H), 2.81 (s, 3H), 2.38 (m, 1H), 2.05 (m, 1H). Anal. Calcd. for $C_{17}H_{18}N_2O_2 \cdot 2.4$ HBr·1.0 $H_2O$: C, 41.29; H, 4.57; N, 5.66; Found: C, 41.37; H, 4.86; N, 5.45.

EXAMPLE 3 trans-4,6-diaza-5,6,6a,7,8,12b-hexahydro-3-propylbenzo[c]phenanthrene 10,11-diol dihydrobromide Following the procedures of Example 1, except substituting 6-propyl-2-pyridinecarboxylic acid (prepared from 2-propylpyridine (Aldrich) according to the procedures of Shuman et al., *J. Org. Chem.*, 55:738–741 (1990)) for the picolinic acid of step 1a, and carrying the product forward as in steps 1a–1d, the title compound was prepared. MS: 311 $(M+H)^+$; $^1H$ NMR $(CD_3OD)$ δ: 8.49 (m, 1H), 7.84 (m, 1H), 6.72 (s, 1H), 6.68 (s, 1H), 4.79 (m, 2H), 4.41 (d, J=11 Hz, 1H), 3.37 (m, 1H), 3.02 (t,J=8 Hz, 2H), 2.98–2.80 (m, 2H), 2.39 (m, 1H), 2.04 (m, 1H), 1.87 (sextet, J=8 Hz, 2H), 1.06 (t, J=8 Hz, 3H). Anal. Calcd. for $C_{19}H_{22}N_2O_2 \cdot 2.2$ HBr·0.7 $H_2O$: C, 45.55; H, 5.15; N, 5.59; Found: C, 45.57; H, 5.35; N, 5.52.

EXAMPLE 4 trans-4,6-diaza-5,6,6a,7,8,12b-hexahydro-3-methoxybenzo[c]phenanthrene 10,11-diol dihydrobromide 4a. 6-methoxypyridine-2-carboxylic acid t-butylamide n-Butyllithium (18.25 mmole) was added dropwise to a cooled solution of 6-bromo-2-methoxypyridine (3.12 g, 16.6 mmole, prepared from 2,6-dibromopyridine (Aldrich) according to Comins and Killpack, *J. Org. Chem.*, 55:69–73 (1990)) in 40 mL of THF at −78° C., the resulting orange solution was stirred for 20 minutes at −78° C., and t-butylisocyanate (26.3 mmole) was added with a syringe. The mixture was stirred for 30 minutes at −78° C., warmed to room temperature, then saturated NH$_4$Cl (20 mL) was added. The layers were separated, and the aqueous layer was extracted with methylene chloride (2×20 mL). The combined organic layers were dried over MgSO$_4$ and concentrated, and the residue was chromatographed on silica gel, eluting with 10% to 25% ethyl acetate in hexane, to provide 2.93 g of the title compound as an oil. MS: 209 (M+H)$^+$; $^1$H NMR (CDCl$_3$) δ: 7.85–7.68 (m, 3H), 6.87 (d, J=8 Hz, 1H), 3.96 (s, 3H), 1.49 (s, 9H).

4b. trans-4,6-diaza-5,6,6a,7,8,12b-hexahydro-3-methoxybenzo[c]phenanthrene 10,11-diol dihydrobromide Following the procedure of Example 1b, except substituting 6-methoxy-2-pyridinecarboxylic acid t-butylamide (prepared in step 4a) for the picolinic acid t-butylamide of step 1b, and carrying the product forward as in steps 1b–1d, the title compound was prepared. MS: 299 (M+H)$^+$; $^1$H NMR (CD$_3$OD) δ: 7.89 (d, J=9 Hz, 1H), 6.89 (d, J=9 Hz, 1H), 6.69 (s, 1H), 6.65 (s, 1H), 4.48 (d, J=16 Hz, 1H), 4.32 (d, J=16 Hz, 1H), 4.16 (d, J=11 Hz, 1H), 3.94 (s, 3H), 3.19 (m, 1H), 2.97 (m, 1H), 2.84 (m, 1H), 2.34 (m, 1H), 1.96 (m, 1H). Anal. Calcd. for C$_{17}$H$_{18}$N$_2$O$_3$.2.4 HBr. 0.8 H$_2$O: C, 40.28; H, 4.37; N, 5.53; Found: C, 40.35; H, 4.43; N, 5.18.

EXAMPLE 5 trans-4,6-diaza-3-fluoro-5,6,6a,7,8,12 b-hexahydrobenzo[c]phenanthrene 10,11-diol dihydrobromide Following the procedures of Example 1, except substituting 6-fluoro-2-pryidinecarboxylic acid (prepared from 2-fluoro-6-methylpyridine (Lancaster Synthesis, Inc.) according to the procedure given by Cooper and Rickard in *Synthesis.*, 1971: 31) for the picolinic acid of step 1a, and carrying the product forward as in steps 1a–1d, the title compound was prepared. MS: 287 (M+H)$^+$. $^1$H NMR (CD$_3$OD) δ: 8.16 (t, J=8 Hz, 1H), 7.16 (dd, J=8 and 3 Hz, 1H), 6.71 (s, 1H), 6.65 (s, 1H), 4.46 (m, 2H), 424 (d, J=11 Hz, 1H), 3.25 (m, 1H), 3.02–2.68 (m, 2H), 2.35 (m, 1H), 1.97 (m, 1H). HRMS Calcd. for C$_{16}$H$_{16}$N$_2$O$_2$F: 287.1196; Found: 287.1197.

EXAMPLE 6 trans-4,6-diaza-5,6,6a,7,8,12b-hexahydrobenzo[c]phenanthrene 3,10,11-triol dihydrobromide Following the procedures of Example 1, except substituting 6-t-butoxy-2-pyridinecarboxylic acid (prepared from 2,6-dibromopyridine (Aldrich) according to the procedure of Comins and Killpack, *J. Org. Chem.*, 55:69–73 (1990)) for the picolinic acid of step 1a, and carrying the product forward as in steps 1a–1d, the title compound is prepared.

EXAMPLE 7 trans-4,6-diaza-5,6,6a,7,8,12b-hexahydro-2-methylbenzo[c]phenanthrene 10,11-diol dihydrobromide Following the procedures of Example 1, except substituting 5-methyl-2-pyridinecarboxylic acid t-butylamide (which was prepared from the corresponding ethyl ester (*Inorg. Syn.*, 1994:4112) according to the procedure of Weinreb et al., *Tetrahedron. Lett.*, 40:4171, 1977)) for the picolinic acid t-butylamide of step 1b, and carrying the product forward as in steps 1a–1d, the title compound was prepared. MS: 283 (M+H)$^+$; $^1$H NMR (CD$_3$OD) δ: 8.45 (s, 1H), 8.10 (s, 1H), 6.54 (s, 1H), 6.52 (s, 1H), 4.52 (m, 2H), 4.20 (d, J=12 Hz, 1H), 3.17 (m, 1H), 2.82–2.60 (m, 2H), 2.36 (s, 3H), 2.18 (m, 1H), 1.83 (m, 1H). Anal. Calcd. for C$_{17}$H$_{18}$N$_2$O$_2$.2.4 HBr.0.9 H$_2$O: C, 41.44; H, 4.54; N, 5.69; Found: C, 41.66; H, 4.77; N, 5.31.

EXAMPLE 8 trans-4,6-diaza-5,6,6a,7,8,12b-hexahydro-2-butylbenzo[c]phenanthrene 10,11-diol dihydrobromide Following the procedures of Example 1, except substituting 5-butyl-2-pyridinecarboxylic acid (Aldrich) for the picolinic acid of step 1a, and carrying the product forward as in steps 1a–1d, the title compound was prepared. MS: 325 (M+H)$^+$; $^1$H NMR (CD$_3$OD) δ: 8.68 (s, 1H), 8.33 (s, 1H), 6.73 (s, 1H), 6.68 (s, 1H), 4.74 (m, 2H), 4.42 (d, J=11 Hz, 1H), 3.36 (m, 1H), 3.0–2.77 (m, 4H), 2.38 (m, 1H), 2.04 (m, 1H), 1.71 (m, 2H), 1.45 (m, 2H), 0.99 (t, J=8 Hz, 3H). Anal. Calcd. for C$_{20}$H$_{24}$N$_2$O$_2$. 2.0 HBr.0.8 H$_2$O: C, 47.98; H, 5.56; N, 5.60; Found: C, 48.16; H, 5.56; N, 5.22.

EXAMPLE 9 trans-4,6 diaza-5,6,6a,7,8,12b-hexahdro-2,3-dimethylbenzo[c]phenanthrene 10,11-diol dihydrobromide Following the procedures of Example 1, except substituting 5,6-dimethyl-2-pyridinecarboxylic acid (prepared from 2,3-lutidine (Aldrich) according to the procedures given by Shuman et al., *J. Org. Chem.*, 55:738–741 (1990) for the picolinic acid of step 1a, and carrying the product forward as in steps 1a–1d, the title compound was prepared. MS: 297 (M+H)$^+$; $^1$H NMR (CD$_3$OD) δ: 8.29 (s, 1H), 6.73 (s, 1H), 6.67 (s, 1H), 4.70 (m, 2H), 4.35 (d, J=11 Hz, 1H), 3.33 (m, 1H), 3.03–2.78 (m, 2H), 2.72 (s, 3H), 2.52 (s, 3H), 2.38 (m, 1H), 2.02 (m, 1H). Anal. Calcd. for C$_{18}$H$_{20}$N$_2$O$_2$. 2.0 HBr.1.5 H$_2$O: C, 44.56; H, 5.19; N, 5.77; Found: C, 44.57; H, 5.02; N, 5.55.

EXAMPLE 10 trans-4,6-diaza-5,6,6a,7,8,12b-hexahydro-2,3-cyclohexenobenzo[c]phenanthrene 10,11-diol dihydrobromide Following the procedures of Example 1, except substituting 5,6-cyclohexeno-2-pyridinecarboxylic acid (prepared from 2,3-cyclohexenopyridine (Aldrich) according to the procedures given by Shuman et al., *J. Org. Chem.*, 55: 738–741 (1990) for the picolinic acid of step 1a, and carrying the product forward as in steps 1a–1d, the title compound was prepared. MS: 323 (M+H)$^+$; $^1$H NMR (CD$_3$OD) δ: 8.32 (s, 1H), 6.73 (s, 1H), 6.68 (s, 1H), 4.76 (m, 2H), 4.40 (d, J=11 Hz, 1H), 3.36 (m, 1H), 3.13 (t, J=6 Hz, 2H), 3.01 (t, J=6 Hz, 2H), 3.00–2.80 (m, 2H), 2.38 (m, 1H), 2.10–1.90 (m, 5H). Anal. Calcd. for C$_{20}$H$_{22}$N$_2$O$_2$.2.0 HBr.1.2 H$_2$O: C, 47.49; H, 5.26; N, 5.54; Found: C, 47.56; H, 5.26; N, 5.21.

EXAMPLE 11 trans-2,6-diaza-5,6,6a,7,8,12b-hexahydrobenzo[c]phenanthrene 10,11-diol dihydrobromide Following the procedures of Example 1, except replacing picolinic acid with isonicotinic acid (Aldrich), the title compound was prepared. MS: 269 (M+H)⁺, 286 (M+NH₄)⁺; ¹H NMR (CD₃OD) δ: 8.91 (s, 1H), 8.87 (d, J=6 Hz, 1H), 8.14 (d, J=6 Hz, 1H), 6.81 (s, 1H), 6.73 (s, 1H), 4.90 (m, 2H), 4.53 (d, J=11, 1H), 3.37 (m, 1H), 2.89 (m, 2H), 2.37 (m, 1H), 2.10–197 (m, 1H). Anal. Calcd. for $C_{16}H_{16}N_2O_2$. 3.0 HBr.1.0 H₂O: C, 36.32; H, 4.00; N, 5.30; Found: C, 36.38; H, 4.20; N, 5.00.

EXAMPLE 12 trans-2,6-diaza-4-fluoro-5,6,6a,7,8,12b-hexahydrobenzo[c]phenanthrene 10,11-diol dihydrobromide 12a. 3-fluoro-4-pyridinecarboxylic acid t-butyl amide Following the procedure of Gribble and Saulnier, *Tetrahedron Lett.*, 21:4137–4140 (1980)) reacting 3-fluoropyridine (Aldrich) with LDA and reacting the 3-fluoro-4-lithiopyridine intermediate with t-butyl isocyanate, the title compound was prepared.

12b. trans-2,6-diaza-4-fluoro-5,6,6a,7,8,12b-hexahydrobenzo[c]phenanthrene 10,11-diol dihydrobromide Following the procedures of Example 1, except replacing picolinic acid t-butylamide of step 1b with the 3-fluoro-4-pyridinecarboxylic acid t-butylamide from step 12a, the title compound was prepared. MS: 287 (M+H)⁺; ¹H NMR (CD₃OD) δ: 8.83 (s, 1H), 8.76 (s, 1H), 6.79 (s, 1H), 6.72 (s, 1H), 4.75 (s, 2H), 4.47 (d, J=11 Hz, 1H), 3.36 (m, 1H), 2.99–2.80 (m, 2H), 2.37 (m, 1H), 2.03 (m, 1H). Anal. Calcd. for $C_{16}H_{15}FN_2O_2$.2.1 HBr.0.5 H₂O: C, 41.31; H, 3.92; N, 6.02; Found: C, 41.37; H, 3.86; N, 5.95.

EXAMPLE 13 trans-3,6-diaza-5,6,6a,7,8,12b-hexahydrobenzo[c] phenanthrene 10,11-diol dihydrobromide 13a. 4-bromo-3-pyridinemethanol Following the procedure of Gribble and Saulnier, *Tetrahedron Lett.*, 21:4137–4140 (1980)) reacting 4-bromopyridine HCl (Aldrich) with 2 eq of LDA, and reacting the 4-bromo-3-lithiopyridine with DMF provided 4-bromo-3-pyridinecarboxaldehyde, which was converted to the title compound by DIBAL reduction. MS: 188 & 190 (M+H)⁺; ¹H NMR (CDCl₃) δ: 8.66 (s, 1H), 8.36 (d, J=6 Hz, 1H), 7.52 (d, J=6 Hz, 1H), 4.82 (d, J=6 Hz, 2H), 2.12 (t, J=6 Hz, 1H).

13b. 4-bromo-3- pyridinylmethyl phenylmethyl ether

The 4-bromo-3-pyridinemethanol from step 13a was benzylated by the standard procedure to afford the title compound. MS: 278 & 280 (M+H)⁺; ¹H NMR (CDCl₃) δ: 8.66 (s, 1H), 8.34 (d, J=5 Hz, 1H), 7.51 (d, J=5 Hz, 1H), 7.43–7.29 (m, 5H), 4.65 (s, 2H), 4.65 (s, 2H).

13c. trans-1,2,3,4-tetrahydro-6,7-dimethoxy-1-(3-(phenylmethoxy)methyl)-4-pyridinyl)-2-nitro-naphthalene n-Butyllithium (2.5 mmole) was added dropwise to a cooled solution of the compound from step 13b above (2.21 mmole) in 20 mL of THF at –78° C., the resultant solution was stirred for 10 minutes at –78° C., and a solution of 1,2-dihydro-6,7-dimethoxy-3-nitronaphthalene (2.26 mmole) in 20 mL of THF, precooled to –78° C., was added via cannula. The mixture was stirred for 1 hour at –78° C., then allowed to warm to room temperature. Saturated NH₄Cl (10 mL) was added, the mixture was allowed to warm to room temperature, and the layers were separated. The aqueous layer was extracted with methylene chloride (4×30 mL). The combined organic solution was dried and concentrated. The residue was dissolved in 15 mL of methanol then 0.5 mL of triethylamine was added, and the solution was stirred at room temperature for 16 hours. The solvent was removed, and the residue was chromatographed on silica gel, eluting with 1:4 to 1:0 ethyl acetate:hexane, to provide 320 mg of the title compound. MS: 435 (M+H)⁺; ¹H NMR (CDCl₃) δ: 8.57 (s, 1H), 8.48 (d, J=5 Hz, 1H), 7.32 (m, 5H), 6.85 (d, J=5 Hz, 1H), 6.61 (s, 1H), 6.19 (s, 1H), 5.13 (d, J=7 Hz, 1H), 4.99 (m, 1H), 470 (d, J=11 Hz, 1H), 4.62 (q, J=11 Hz, 2H), 4.58 (d, J=11 Hz, 1H), 3.87 (s, 3H), 3.48 (s, 3H), 3.04–2.86 (m, 2H), 2.51–2.29 (m, 2H).

13d. trans-1,2,3,4-tetrahydro-6,7-dimethoxy-1-(3-hydroxymethyl-4-pyridinyl)-2-nitro-naphthalene The title compound was prepared from the compound of step 13c by a standard hydrogenolysis procedure (H₂, 10% Pd/C, ethanol). MS: 345 (M+H)⁺; ¹H NMR (CDCl₃) δ: 8.61 (s, 1H), 8.50 (d, J=5 Hz, 1H), 6.89 (d, J=5 Hz, 1H), 6.64 (s, 1H), 6.17 (s, 1H), 5.17 (d, J=7 Hz, 1H), 5.09 (m, 1H), 4.83 (d, J=5 Hz, 2H), 3.88 (s, 3H), 3.61 (s, 3H), 3.10–2.91 (m, 2H), 2.56–2.36 (m, 2H), 2.04 (t, J=5 Hz, 1H).

13e. trans-1,2,3,4-tetrahydro-6,7-dimethoxy-1-3-hydroxymethyl-4-pyridinyl)-2-naphthaleneamine The compound of step 13d was treated with Zn dust (2–5 equivalents) and 6N HCl in ethanol. The mixture was made basic by addition of saturated NaHCO₃. NaCl (20 g) was added, the mixture stirred vigorously for 20 minutes, and the solids were removed by filtration. The filtrate was extracted with methylene chloride, the organic extract was dried MgSO₄ and concentrated, and the residue was purified to afford the title compound. MS: 345 (M+H)⁺; ¹H NMR (CDCl₃) δ: 8.57 (s, 1H), 8.39 (d, J=5 Hz, 1H), 6.99 (d, J=5 Hz, 1H), 6.78 (s, 1H), 6.20 (s, 1H), 4.83 (s, 2H), 4.43 (d, J=8 Hz, 1H), 3.82 (s, 3H), 3.53 (s, 3H), 3.47 (m, 1H), 3.11–2.88 (m, 2H), 2.22–2.12 (m, 1H), 1.95–1.80 (m, 1H).

13f. trans-N-BOC-1,2,3,4-tetrahydro-6,7-dimethoxy-1-(3-hydroxymethyl-4-pyridinyl)-2-naphthaleneamine To a solution of the compound from step 13e (2.67 mmole) in 40 mL of DMF cooled to 0° C. were added triethylamine (1 mL) and di-t-butyl dicarbonate (3.11 mmole). The mixture was stirred for 5 minutes at 0° C. and for an hour at room temperature. Water (20 mL) was added, and the mixture was partitioned between methylene chloride and water. The combined organic extracts were dried MgSO₄), and the residue was chromatographed on silica gel, eluting with 5% methanol containing 5% NH₄OH in methylene chloride, to afford 0.832 g of the title compound. MS: 415 (M+H)⁺; ¹H NMR (CDCl₃) δ: 8.58 (s, 1H), 8.39 (d, J=5 Hz, 1H), 6.69 (d, J=5 Hz, 1H), 6.67 (s, 1H), 6.16 (s, 1H), 5.12 (d, J=8 Hz, 1H), 4.99 (m, 1H), 4.75 (m, 1H), 4.59 (m, 1H), 4.44 (m, 1H), 4.14 (m, 1H), 3.89 (s, 3H), 3.66 (s, 3H), 3.0 (m, 1H), 2.85 (m, 1H), 2.10 (m, 1H), 1.75 (m, 1H), 1.39 (s, 9H).

13g. trans-N-BOC-1,2,3,4-tetrahydro-6,7-dimethoxy-1-(3-chloromethyl-4-pyridinyl)-2-naphthaleneamine The compound from step 13f (1.87 mmole) was dissolved in 50 mL of methylene chloride, and the solution was cooled to –10° C. Triethylamine (7.17 mmole) and methanesulfonyl chloride (3.88 mmole) were added, and the mixture was stirred at –10° C. for 30 minutes. After the solvent was removed, the residue was dissolved in 30 mL of DMF, LiCl (0.8 g) was added, and the mixture was stirred at room temperature for 18 hours. Saturated NaHCO₃ (20 mL) was added, and the mixture was partitioned between ether and water. The combined organic extracts were dried (MgSO₄), and the solvent was removed. The residue was taken directly to the next step without further purification. MS: 433 (M+H)⁺; ¹H NMR (CDCl₃) δ: 8.59 (s, 1H), 8.42 (d, J=5 Hz, 1H), 6.76 (d, J=5 Hz, 1H), 6.67 (s, 1H), 6.24 (s, 1H), 5.34 (d, J=12 Hz, 1H), 4.86 (m, 1H), 4.70 (d, J=12 Hz, 1H), 4.46 (m, 1H), 3.99 (m, 1H), 3.89 (s, 3H), 3.66 (s, 3H), 3.00 (m, 1H), 2.85 (m, 1H), 2.03 (m, 1H), 1.84 (m, 1H), 1.39 (s, 9H).

13h. trans-3,6-diaza-5,6,6a,7,8,12b-hexahydro-10,11-dimethoxybenzo[c]phenanthrene The compound from step 13g was treated with a solution of HCl in dioxane (4.0M, 20 mL, 80 mmole). The mixture was stirred for 1 hour at room temperature, solvent was removed under vacuum, and the remaining solid was suspended in 100 mL of t-butanol. $K_2CO_3$ (2.2 g) and NaI (1 g) were added, and the mixture was heated at reflux for 3 hours. After cooling the solution to room temperature, the solvent was removed, methylene chloride was added, and the solid was removed by filtration. The filtrate was concentrated, and the residue was chromatographed on silica gel, eluting with 5–15% methanol containing 5% $NH_4OH$ in methylene chloride, to afford 350 mg of the title compound. MS: 297 (M+H)$^+$; $^1$H NMR (CDCl$_3$) δ: 8.51 (d, J=5 Hz, 1H), 8.44 (s, 1H), 7.41 (d, J=5 Hz, 1H), 6.83 (s, 1H), 6.75 (s, 1H), 4.13 (s, 2H), 3.89 (s, 3H), 3.82 (d, J=9 Hz, 1H), 3.80 (s, 3H), 3.00–2.70 (m, 3H), 2.20 (m, 1H), 1.75 (m, 1H).

13i. trans-3,6-diaza-5,6,6a,7,8,12b-hexahydrobenzo[c]phenanthrene 10,11-diol dihydrobromide Applying the procedure of Example 1d to the compound of step 13h above, the title compound was prepared. MS: 269 (M+H)$^+$; $^1$H NMR (CD$_3$OD) δ: 8.99 (s, 1H), 8.86 (d, J=6 Hz, 1H), 8.13 (d, J=6 Hz, 1H), 6.79 (s, 1H), 6.72 (s, 1H), 4.77 (m, 2H), 4.58 (d, J=11 Hz, 1H), 3.26 (m, 1H), 2.86 (m, 2H), 2.37 (m, 1H), 2.13–2.00 (m, 1H). Anal. Calcd. for $C_{16}H_{16}N_2O_2 \cdot 2.7$ HBr$\cdot 0.8$ H$_2$O: C, 38.34; H, 4.08; N, 5.59; Found: C, 38.43; H, 4.22; N, 5.23.

EXAMPLE 14 trans-2,6-diaza-4-methyl-5,6,6a,7,8,12b-hexahydrobenzo[c]phenanthrene 10,11-diol dihydrobromide 14a. 3,5-dibromo-4-pyridinemethanol Following the procedure of Gribble and Saulnier, (*Tetrahedron Lett.*, 21:4137–4140 (1980)) reacting 3,5-bromopyridine (Aldrich) with LDA, and reacting the 3,5-dibromo-4-lithiopyridine with DMF provided 3,5-dibromo-4-pyridinecarboxaldehyde, which was then converted to the title compound by DIBAL reduction. $^1$H NMR (CDCl$_3$) δ: 8.65 (s, 2H), 4.97 (s, 2H), 2.32 (s, br, 1H).

14b. 3,5-dibromo-4-pyridinemethyl methoxymethyl ether

Reacting the compound from step 14a with methoxymethyl chloride by standard procedures gave the title compound. $^1$H NMR (CDCl$_3$) δ: 8.66 (s, 2H), 4.85 (s, 2H), 4.77 (s, 2H), 3.45 (s, 3H).

14c. (3-bromo-5-methyl-4-pyridyl)methyl methoxymethyl ether n-Butyllithium (8.4 mole) was added to a cooled solution of the compound from step 14b (8.0 mmole) in 100 mL of THF at −78° C., the mixture was stirred for 5 minutes at −78° C., then methyl iodide (10 mmole) was added. Stirring was continued for 10 minutes at −78° C., saturated NH$_4$Cl (20 mL) was added, and the mixture was warmed to room temperature. The mixture was partitioned between ether and water, the organic extracts were dried MgSO$_4$) and concentrated, and the residue was passed through a pad of silica gel, washing with 10% ethyl acetate in hexane, to provide 1.45 g of the title compound. $^1$H NMR (CDCl$_3$) δ: 8.59 (s, 1H), 8.34 (s, 1H), 4.75 (s, 2H), 4.72 (s, 2H), 3.43 (s, 3H), 2.45 (s, 3H).

14d. trans-1,2,3,4-tetrahydro-6,7-dimethoxy-1-(4-hydroxymethyl-5-methyl-3-pyridinyl)-2-nitro-naphthalene The compound of step 14c was condensed with 1,2-dihydro-6,7-dimethoxy-3-nitronaphthalene according to the procedure of Example 13c. The protecting methoxymethyl group was removed from the intermediate by a standard hydrolysis method (HCl, ethanol).

14e. trans-2,6-diaza-4-methyl-5,6,6a,7,8,12b-hexahydrobenzo[c]phenanthrene 10,11-diol dihydrobromide Following the procedure of Example 13e above, replacing the compound of example 13d with the compound of step 14d above, and carrying the product forward according to the steps 13f through 13i, the title compound was prepared. MS: 283 (M+H)$^+$; $^1$H NMR (CD$_3$OD) δ: 8.78 (s, 1H), 8.75 (s, 1H), 6.76 (s, 1H), 6.73 (s, 1H), 4.79 (s, 2H), 4.49 (d, J=11 Hz, 1H), 3.36 (m, 1H), 2.90 (m, 2H), 2.57 (s, 3H), 2.38 (m, 1H), 2.10–1.96 (m, 1H). Anal. Calcd. for $C_{17}H_{18}N_2O_2 \cdot 3.1$ HBr$\cdot 0.7$ methanol: C, 38.26; H, 4.34; N, 5.04; Found: C, 38.50; H, 4.16; N, 4.73.

EXAMPLE 15 trans-3,6-diaza-4-fluoro-5,6,6a,7,8,12b-hexahydro-2-methylbenzo[c]phenanthrene 10,11-diol dihydrobromide 4-Bromo-2-fluoro-6-methyl-3-pyridinemethanol is prepared two steps from commercially available 2-fluoro-6-methylpyridine (Lancaster Synthesis Inc.) by following the procedure of Queguiner (*J. Org. Chem.*, 57:565–573, 1992 and references cited therein). Following the procedures of Example 13, substituting 4-bromo-2-fluoro-6-methyl-3-pyridinemethanol for the 4-bromo-3-pyridinemethanol of step 13a thereof, and carrying the product, the title compound is prepared.

EXAMPLE 16 trans-3,6-diaza-4-chloro-5,6,6a,7,8,12b-hexahydro-2-methylbenzo[c]phenanthrene 10,11-diol dihydrobromide 4-Bromo-2-chloro-6-methyl-3-pyridinemethanol is prepared in two steps from commercially available 2-chloro-6-methylpyridine (Lancaster Synthesis Inc.) by following the procedure of Queguiner (*J. Org. Chem.*, 57:565–573, 1992 and references cited therein). Following the procedures of Example 13, substituting 4-bromo-2-chloro-6-methyl-3-pyridinemethanol for the 4-bromo-3-pyridinemethanol of step 13a thereof, and carrying the product, the title compound is prepared.

BIOLOGICAL STUDIES

Radioligand binding studies: Human clones.

Protocols for membrane preparations of HEK-D$_1$ and LTK-D$_2$(short) receptors were as described previously [Lin et al, *Mol. Pharmacol.* 47, 131–139, 1995 and Kebabian et al, *Eur. J. Pharmacol.*, 229, 203–209, 1992]. For the human D$_1$ receptor assay, 40 µg of protein were incubated with [$^3$H]-SCH 23390 (0.9 nM, K$_d$=0.84 nM), in the presence and absence of competitor, at room temperature for 40 min. SCH 23390 (1 µM) was used to define non-specific binding for D$_1$ receptor. For the D$_2$ receptor assay, 50 µg of membrane protein were incubated with [$^3$H]-spiperone (0.7 nM, K$_d$=0.08 nM), with and without competitor, at 37° C. for 20 min. Non-specific binding at D$_2$ receptor was defined with 100 µM (+)-butaclamol. Binding experiments were terminated by filtration with a Skatron Micro96 Cell Harvester (Skatron, Sterling, Va.). The amount of radioactive tritium and iodide, trapped on #32 glass fiber mats (Schleicher & Schuell, Keene, N.H.), was determined by a LKB 1205 Betaplate counter (Gaithersburg, Md.) or Parkard Cobra Auto-Gamma counter (Meriden, Conn.), respectively. The $IC_{50}$ values for the compounds of this invention were determined from the competition studies by Hill analysis, and $K_i$ values were then calculated using the Cheng-Prusoff equation. These data are shown below in Table 1, under the columns headed hD1 and hD2, wherein lower $K_i$ is indicative of higher dopaminergic binding activity.

Adenylate cyclase activity: Human $D_1$ receptor.

The interaction of dopamine or a dopamine D-1 receptor agonist with the D-1 receptor causes a dose-dependent increase in the adenylate cyclase-catalyzed conversion of adenosine triphosphate (ATP) to cyclic adenosine monophosphate (cAMP). The functional activity of the compounds of the invention was determined by assaying their ability to either stimulate the enzyme adenylate cyclase to produce cAMP (agonist activity). Assays were conducted in 24-well or 48-well tissue culture plates. The assay buffer consisted of DPBS containing $CaCl_2$ and $MgCl_2$, 0.1% glucose, 0.5 mM IBMX, 0.004% ascorbic acid and 10 μM propranolol to inhibit potential cross activation of the endogenous β-receptor. Culture medium was removed, and HEK-$D_1$ cell was washed once with assay buffer, and 400 μl fresh assay buffer was added for 10 min. Next, 100 μl of dopamine or dopamine agonist, dissolved in assay buffer, was added to the cell for an additional 15 min, and incubations were terminated with 500 μL 0.2N HCl. cAMP contents were determined by RIA using the automated Attoflo™ system (Rockville, Md.).

$ED_{50}$ values and relative intrinsic activities to dopamine of the compounds of this invention in human $D_1$ receptor were calculated from dose-response curves using the stimulatory response of 10 μM DA as 100%. These data are shown below in Table 1, under the columns headed hD1c $ED_{50}$ and IA. The hD1c $ED_{50}$ level is a measure of the potency, showing the concentration (nM) at which a 50% response is obtained; a lower number indicates a higher potency. High intrinsic activity (IA) indicates the activity of the compound as a dopamine agonist.

TABLE 1

Competitive Binding

| Example # | hD1 (nM) | hD2 (nM) | hD1c ED50 (nM) | IA (%) |
|---|---|---|---|---|
| 1 | 65 | 2500 | 6.7 | 125 |
| 2 | 140 | 1400 | 23 | 121 |
| 3 | 45 | 450 | 8.6 | 116 |
| 4 | 49 | 520 | 8.8 | 114 |
| 5 | 180 | 2200 | 18 | 141 |
| 7 | 240 | 12000 | 110 | 156 |
| 8 | 890 | 1900 | 180 | 118 |
| 9 | 280 | 9100 | 120 | 134 |
| 10 | 560 | 3600 | 63 | 136 |
| 11 | 1100 | 1300 | 320 | 81 |
| 12 | 390 | 890 | 800 | 126 |
| 13 | 140 | 4400 | 38 | 131 |
| 14 | 1100 | 400 | 230 | 75 |

Rotation Behavior

The behavioral assay used was based on the rat rotational model. Striatal dopamine was depleted by the intracranial injection of 6-hydroxydopamine, a neurotoxin which specifically destroys catecholaminergic neurons. The intracranial injection was conducted on anesthetized animals using standard stereotaxic techniques (U. Ungerstedt and G. W. Arbuthnott, Brain Research, 24:485, 1970, and U. Ungerstedt, Acta Physiol. Scand. Suppl. 367, 69:1973). This unilateral lesioning of dopamine-containing neurons causes the post-synaptic dopamine receptors to become supersensitive to dopaminergic stimulation in behavioral assays. When these striatal dopamine receptors are stimulated by the test compounds, the rats rotate, or turn, in a direction that is away from the side of their body that receives the greater dopaminergic activation due to the receptor supersensitivity, i.e., animals turn away from the lesioned side of the brain when given a direct-acting dopamine agonist. Agonist activity was measured by the ability of the test compound to induce rotation.

Table 2 below shows the rotation behavior, measured as the potency of the compound to act as a dopamine agonist, of selected compounds of the present invention. A lower number indicates a higher potency.

TABLE 2

Rotation Behaviou

| Example # | $EC_{50}$ (μmol/kg)sc |
|---|---|
| 3 | 0.14 |
| 5 | 0.82 |

We claim:

1. The compound having the formula:

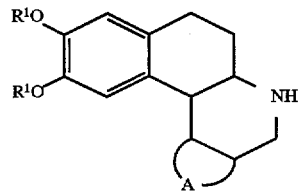

or a pharmaceutically-acceptable salt, ester, carbamate or prodrug thereof, wherein:
$R^1$ is hydrogen or a readily-cleavable group;
A and the atoms to which it is attached comprise a pyridine ring selected from the group consisting of:

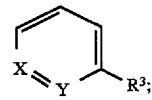

(a) and

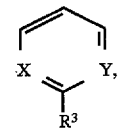

wherein
one of X and Y is N and the other is $CR^2$, and
$R^2$ and $R^3$ are independently selected from the group consisting of
hydrogen, Cl, Br, F, $C_1$–$C_6$-alkyl, $C_1$–$C_6$-alkoxy or $C_1$–$C_6$-haloalkyl; or additionally, one of $R^2$ and $R^3$ may be $C_3$–$C_7$-cycloalkyl; or when on adjacent carbon atoms $R^2$ and $R^3$ may be taken together with the atoms to which they are attached to form a $C_5$–$C_7$-cycloalkene ring.

2. The compound according to claim 1 wherein $R^1$ is as defined above and A and the atoms to which it is attached comprise a pyridine ring having the formula:

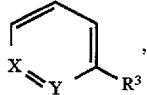

wherein one of X and Y is N and the other is $CR^2$, and $R^2$ and $R^3$ are independently selected from the group consisting of hydrogen, Cl, Br, F, $C_1$–$C_6$-alkyl, $C_1$–$C_6$-alkoxy or $C_1$–$C_6$-haloalkyl; or additionally, one of $R^2$ and $R^3$ may be $C_3$–$C_7$-cycloalkyl.

3. The compound according to claim 1 wherein $R^1$ is as defined above and A and the atoms to which it is attached comprise a pyridine ring having the formula:

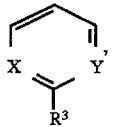

wherein one of X and Y is N and the other is $CR^2$, and $R^2$ and $R^3$ are independently selected from the group consisting of hydrogen, Cl, Br, F, $C_1$–$C_6$-alkyl, $C_1$–$C_6$-alkoxy, $C_1$–$C_6$-alkoxy or $C_1$–$C_6$-haloalkyl; or additionally, one of $R^2$ and $R^3$ may be $C_3$–$C_7$-cycloalkyl.

4. The compound according to claim 1 wherein $R^1$ is as defined above and A and the atoms to which it is attached comprise a pyridine ring selected from:

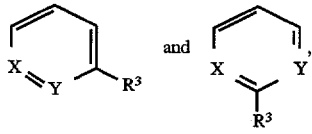

wherein one of X and Y is N and the other is $CR^2$, and $R^2$ and $R^3$ are on adjacent carbon atoms and are taken together with the atoms to which they are attached to form a $C_5$–$C_7$-cycloalkene ring.

5. The compound according to claim 1 wherein $R^1$ is as defined above and A and the atoms to which it is attached comprise a pyridine ring having the formula:

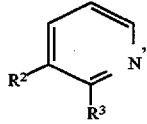

wherein $R^2$ and $R^3$ are independently selected from the group consisting of hydrogen, Cl, Br, F, $C_1$–$C_6$-alkyl, $C_1$–$C_6$-alkoxy or $C_1$–$C_6$-haloalkyl.

6. The compound according to claim 1 wherein $R^1$ is as defined above and A and the atoms to which it is attached comprise a pyridine ring having the formula:

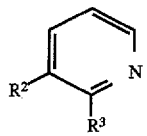

wherein $R^2$ is hydrogen and $R^3$ is F or n-propyl.

7. A compound according to claim 1, which is:
trans-4,6-diaza-5,6,6a,7,8,12b-hexahydrobenzo[c]phenanthrene 10,11-diol;
trans-4,6-diaza-5,6,6a,7,8,12b-hexahydro-3-methylbenzo[c]phenanthrene 10,11-diol;
trans-4,6-diaza-5,6,6a,7,8,12b-hexahydro-3-propylbenzo[c]phenanthrene 10,11-diol;
trans-4,6-diaza-5,6,6a,7,8,12b-hexahydro-3-methoxybenzo[c]phenanthrene 10,11-diol;
trans-4,6-diaza-3-fluoro-5,6,6a,7,8,12b-hexahydrobenzo[c]phenanthrene 10,11-diol;
trans-4,6-diaza-5,6,6a,7,8,12b-hexahydrobenzo[c]phenanthrene 3,10,11-triol;
trans-4,6-diaza-5,6,6a,7,8,12b-hexahydro-2-methylbenzo[c]phenanthrene 10,11-diol;
trans-4,6-diaza-5,6,6a,7,8,12b-hexahydro-2-butylbenzo[c]phenanthrene 10,11-diol;
trans-4,6-diaza-5,6,6a,7,8,12b-hexahydro-2,3-dimethylbenzo[c]phenanthrene 10,11-diol;
trans-4,6-diaza-5,6,6a,7,8,12b-hexahydro-2,3-cyclohexenobenzo[c]phenanthrene 10,11-diol;
trans-2,6-diaza-5,6,6a,7,8,12b-hexahydrobenzo[c]phenanthrene 10,11-diol;
trans-2,6-diaza-4-fluoro-5,6,6a,7,8,12b-hexahydrobenzo[c]phenanthrene 10,11-diol;
trans-3,6-diaza-5,6,6a,7,8,12b-hexahydrobenzo[c]phenanthrene 10,11-diol;
trans-2,6-diaza-4-methyl-5,6,6a,7,8,12b-hexahydrobenzo[c]phenanthrene 10,11-diol;
trans-3,6-diaza-4-fluoro-5,6,6a,7,8,12b-hexahydro-2-methylbenzo[c]phenanthrene 10,11-diol; or
trans-3,6-diaza-4-chloro-5,6,6a,7,8,12b-hexahydro-2-methylbenzo[c]phenanthrene 10,11-diol.

8. A compound according to claim 1, which is:
trans-4,6-diaza-5,6,6a,7,8,12b-hexahydrobenzo[c]phenanthrene 10,11-diol;
trans-4,6-diaza-5,6,6a,7,8,12b-hexahydro-3-methylbenzo[c]phenanthrene 10,11-diol;
trans-4,6-diaza-5,6,6a,7,8,12b-hexahydro-3-propylbenzo[c]phenanthrene 10,11-diol;
trans-4,6-diaza-5,6,6a,7,8,12b-hexahydro-3-methoxybenzo[c]phenanthrene 10,11-diol;
trans-4,6-diaza-3-fluoro-5,6,6a,7,8,12b-hexahydrobenzo[c]phenanthrene 10,11-diol;
trans-4,6-diaza-5,6,6a,7,8,12b-hexahydrobenzo[c]phenanthrene 3,10,11-triol;
trans-4,6-diaza-5,6,6a,7,8,12b-hexahydro-2-methylbenzo[c]phenanthrene 10,11-diol;
trans-4,6-diaza-5,6,6a,7,8,12b-hexahydro-2-butylbenzo[c]phenanthrene 10,11-diol;
trans-4,6-diaza-5,6,6a,7,8,12b-hexahydro-2,3-dimethylbenzo[c]phenanthrene 10,11-diol; or
trans-4,6-diaza-5,6,6a,7,8,12b-hexahydro-2,3-cyclohexenobenzo[c]phenanthrene 10,11-diol.

9. A compound according to claim 1, which is:
trans-4,6-diaza-5,6,6a,7,8,12b-hexahydro-3-propylbenzo[c]phenanthrene 10,11-diol; or
trans-4,6-diaza-3-fluoro-5,6,6a,7,8,12b-hexahydrobenzo[c]phenanthrene 10,11-diol.

10. A pharmaceutical composition for selectively binding and activating dopaminergic receptors comprising a pharmaceutically-acceptable carrier and a therapeutically-effective amount of a compound according to claim 1.

11. A pharmaceutical composition for selectively binding and activating dopaminergic receptors comprising a pharmaceutically-acceptable carrier and a therapeutically-effective amount of a compound according to claim 5.

12. A pharmaceutical composition for selectively binding and activating dopaminergic receptors comprising a pharmaceutically-acceptable carrier and a therapeutically-effective amount of a compound according to claim 6.

13. A method for treating dopamine-related neurological, psychological, cardiovascular, cognitive or attention disorders, substance abuse or addictive behavior, or a combination of these indications, in a patient having abnormal dopaminergic activity, comprising administering to the patient in need of such treatment a therapeutically-acceptable amount of a compound according to claim 1.

14. A method for treating dopamine-related neurological, psychological, cardiovascular, cognitive or attention disorders, substance abuse or addictive behavior, or a combination of these indications, in a patient having abnormal dopaminergic activity, comprising administering to the patient in need of such treatment a therapeutically-acceptable amount of a compound according to claim 5.

15. A method for treating dopamine-related neurological, psychological, cardiovascular, cognitive or attention disorders, substance abuse or addictive behavior, or a combination of these indications, in a patient having abnormal dopaminergic activity, comprising administering to the patient in need of such treatment a therapeutically-acceptable amount of a compound according to claim 6.

16. A process for the preparation of a compound having the formula

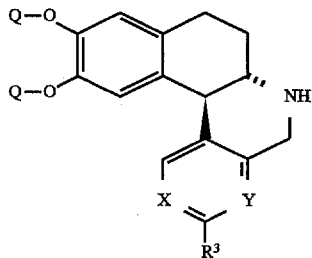

wherein Q is a protecting group and one of X and Y is N and the other is $CR^2$, wherein $R^2$ and $R^3$ are independently selected from the group consisting of hydrogen, Cl, Br, F, $C_1-C_6$-alkyl, $C_1-C_6$-alkoxy or $C_1-C_6$-haloalkyl;
the method comprising
reacting a compound having the formula

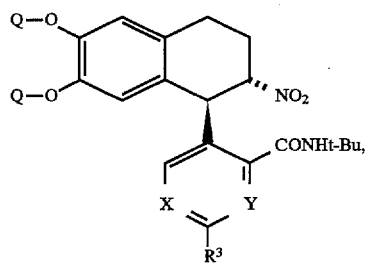

wherein Q, X, Y, $R^2$ and $R^3$ are as above with an excess of zinc dust and aqueous HCl, and isolating the product compound.

17. The process according to claim 16 wherein X is $CR^2$ and Y is N.

18. The process according to claim 16 wherein X is N and Y is $CR^2$.

19. A process according to claim 16 for the preparation of trans-diaza-5,6,6a,7,8,12b-hexahydro-benzo[c]phenanthrene 10,11-diols having the Formula

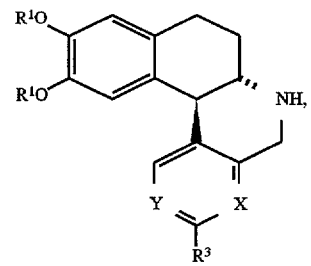

wherein $R^1$ is hydrogen or a readily-cleavable group and X=N and Y=$CR^2$ or Y=N and X=$CR^2$, wherein $R^2$ and $R^3$ are independently selected from the group consisting of hydrogen, Cl, Br, F, $C_1-C_6$-alkyl, $C_1-C_6$-alkoxy or $C_1-C_6$-haloalkyl;

the method comprising:
(a) treating a compound having the formula

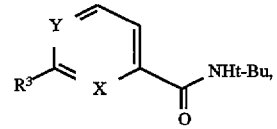

wherein X, Y, $R^2$ and $R^3$ are as defined above, with two equivalents of a strong base alkyllithium reagent at –78° C. for 30 minutes, followed by reaction with a compound having the formula

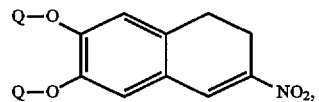

wherein Q is a protecting group selected from the group consisting of an ether moiety, an alkoxyalkyl ether moiety, an alkylthioalkyl ether moiety, tetrahydropyranyl, arylalkyl, a trialkylsilyl ether moiety, a cyclic acetal moiety and a cyclic ketal moiety, followed by treatment with a weak base in a solvent selected from methanol, ethanol or acetonitrile, and isolating the product compound having the formula

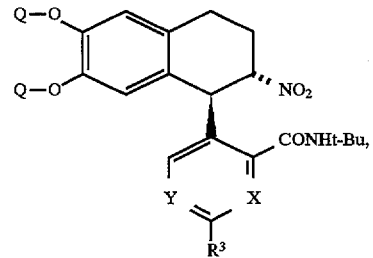

wherein Q, X, Y, $R^2$ and $R^3$ are as above;

(b) reacting the compound of step (a) with an excess of zinc dust and HCl, and isolating the product compound having the formula

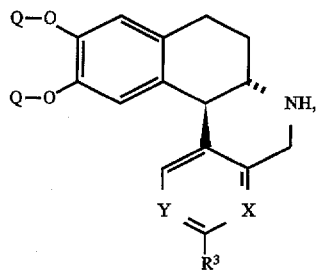

wherein Q, X, Y, $R^2$ and $R^3$ are as above;

(c) deprotecting the compound of step (b) by treatment with $BBr_3$ in a chlorinated solvent at $-78°$ C. to room temperature and isolating the product compound wherein $R^1$ is hydrogen and X, Y, $R^2$ and $R^3$ are as above.

20. The process according to claim 19 wherein X is $CR^2$ and Y is N.

21. The process according to claim 19 wherein X is N and Y is $CR^2$.

22. A process for the preparation of trans-diaza-5,6,6a,7,8,12b-hexahydro-benzo[c]phenanthrene 10,11-diols having the Formula

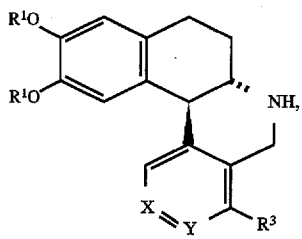

wherein $R^1$ is hydrogen or a readily-cleavable group, wherein X=N and Y=$CR^2$ or Y=N and X=$CR^2$, and $R^2$ and $R^3$ are independently selected from the group consisting of hydrogen, Cl, Br, F, $C_1$-$C_6$-alkyl, $C_1$-$C_6$-alkoxy or $C_1$-$C_6$-haloalkyl;

the method comprising:
(a) treating a compound having the formula

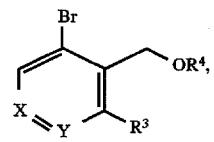

wherein X=N and Y=$CR^2$ or Y=N and X=$CR^2$, $R^2$ and $R^3$ are as defined above, and $R^4$ is a protecting group with a strong base alkyllithium reagent at $-78°$ C. for 30 minutes, followed by reaction with a compound having the formula

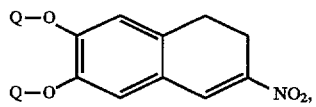

wherein Q is a protecting group selected from the group consisting of an ether moiety, an alkoxyalkyl ether moiety, an alkylthioalkyl ether moiety, tetrahydropyranyl, arylalkyl, a trialkylsilyl ether moiety, a cyclic acetal moiety and a cyclic ketal moiety, followed by treatment with a weak base in a solvent selected from methanol, ethanol or acetonitrile, and isolating the product compound having the formula

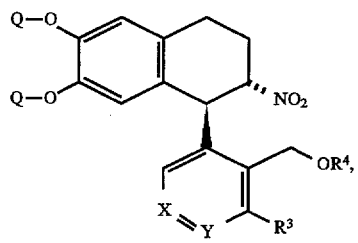

wherein Q, X, Y, $R^2$, $R^3$ and $R^4$ are as above;

(b) removing the $R^4$ grouping from the compound of step (a) by treatment with a reagent selected from HCl when $R^4$ is THP, and MOM or hydrogenolysis with Pd/C when $R^4$ is benzyl, followed by reducing the nitro group with zinc dust and a strong acid, protecting the newly formed amine by reaction with di-t-butyl-dicarbonate and isolating the product compound having the formula

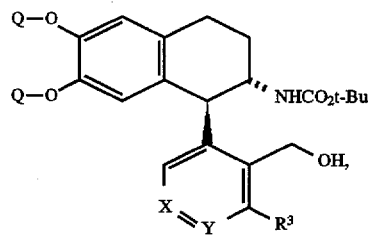

wherein Q, X, Y, $R^2$ and $R^3$ are as above;

(c) treating the compound of step (b) with methanesulfonyl chloride in TEA to convert the hydroxyl group to a methanesulfonyl group, reacting the methanesulfonyl group with LiCl in DMF to replace the methanesulfonyl group with a chlorine atom, then deprotecting the protected-amino group of this compound by treatment with HCl, and cyclizing the deprotected compound by treatment with $K_2CO_3$ in t-butanol at reflux to give the compound

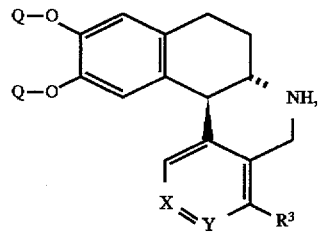

(d) deprotecting the compound of step (c) by treatment with $BBr_3$ in a chlorinated solvent at $-78°$ C. to room temperature and isolating the product compound wherein $R^1$ is hydrogen and X, Y, $R^2$ and $R^3$ are as above.

23. The process according to claim 22 wherein X is $CR^2$ and Y is N.

24. The process according to claim 22 wherein X is N and Y is $CR^2$.

* * * * *